US010526642B2

(12) United States Patent
Molloy et al.

(10) Patent No.: US 10,526,642 B2
(45) Date of Patent: Jan. 7, 2020

(54) DNA METHYLATION IN COLORECTAL AND BREAST CANCER DIAGNOSTIC METHODS

(75) Inventors: Peter Laurence Molloy, Chatswood (AU); Lawrence Charles Lapointe, West Pennant Hills (AU); Susanne Kartin Pedersen, Sydney (AU); Susan Margaret Mitchell, Sydney (AU)

(73) Assignees: Commonwealth Scientific and Industrial Research Organisation, Campbell (AU); Clinical Genomics Pty. Ltd., North Ryde (AU)

( * ) Notice: Subject to any disclaimer, the term of this patent is extended or adjusted under 35 U.S.C. 154(b) by 365 days.

(21) Appl. No.: 14/240,734

(22) PCT Filed: Aug. 24, 2012

(86) PCT No.: PCT/AU2012/000999
§ 371 (c)(1),
(2), (4) Date: Jun. 30, 2014

(87) PCT Pub. No.: WO2013/026104
PCT Pub. Date: Feb. 28, 2013

(65) Prior Publication Data
US 2014/0315203 A1    Oct. 23, 2014

Related U.S. Application Data

(60) Provisional application No. 61/527,503, filed on Aug. 25, 2011.

(51) Int. Cl.
C12Q 1/68        (2018.01)
C12Q 1/6816    (2018.01)
C12Q 1/6886    (2018.01)

(52) U.S. Cl.
CPC ......... *C12Q 1/6816* (2013.01); *C12Q 1/6886* (2013.01); *C12Q 2600/154* (2013.01)

(58) Field of Classification Search
CPC ............ C12Q 1/6886; C12Q 2600/112; C12Q 2600/154; C12Q 1/6816; G01N 2800/06
See application file for complete search history.

(56) References Cited

U.S. PATENT DOCUMENTS

| 5,786,146 | A | 7/1998 | Herman et al. |
| 2004/0241651 | A1 | 12/2004 | Olek et al. |
| 2005/0069879 | A1 | 3/2005 | Berlin |
| 2009/0191548 | A1 | 7/2009 | Berlin et al. |
| 2011/0183924 | A1 | 7/2011 | Mintz et al. |
| 2015/0141275 | A1* | 5/2015 | Molloy ................ C12Q 1/6886 506/9 |
| 2015/0152505 | A1* | 6/2015 | Lapointe .............. C12Q 1/6886 435/6.11 |

FOREIGN PATENT DOCUMENTS

| CN | 101688239 A | 3/2010 |
| WO | WO 00/70090 A1 | 11/2000 |
| WO | WO 02/00928 A2 | 1/2002 |
| WO | WO 2008/100913 A2 | 8/2008 |

OTHER PUBLICATIONS

GenBank Locus AL356119 (Jan. 13, 2009), from www.ncbi.nlm.nih.gov, printed pp. 1-26.*
Sandoval, J. et al. Epigenetics 6:6, 692-702; Jun. 1, 2011.*
Costello, J.F. et al. The Journal of Biological Chemistry (1994), vol. 269, No. 25. pp. 17228-17237.*
Juppner H. Bone, vol. 17, No. 2, Supp., Aug. 1995, 39S-42S.*
Vaissiere T. et al. Epigenetics (2009), 4:4, 221-230.*
Weisenberger, D.J. et al (2008) Comprehensive DNA Methylation Analysis on the Illumina Infinium Assay Platform, Application Note: Epigenetic Analysis, pp. 1-4.*
Le J. et al. Proceedings of the 102nd Annual Meeting of the American Association for Cancer Research; Apr. 2-6, 2011; Orlando, FL. Philadelphia (PA): AACR; Cancer Res 2011;71(8 Suppl):Abstract nr LB-178.*
Infinium HumanMethylation450K BeadChip Support—Downloads, orinted on Jun. 21, 2017 from https://support.illumina.com.*
Abrams, Ezra S. et al., "Use of Denaturing Gradient Gel Electrophoresis to Study Conformational Transitions in Nucleic Acids" Methods in Enzymology, 1992, pp. 71-104, vol. 212.
Adams, Steven P. et al., "Hindered Dialkylamino Nucleoside Phosphite Reagents in the Synthesis of Two DNA 51-Mers" J. Am. Chem. Soc., 1983, pp. 661-663, vol. 105, No. 3.
Alon, U. et al., "Broad patterns of gene expression revealed by clustering analysis of tumor and normal colon tissues probed by oligonucleotide arrays" Proc. Natl. Acad. Sci. USA, Jun. 1999, pp. 6745-6750, vol. 96.

(Continued)

*Primary Examiner* — Stephen T Kapushoc
(74) *Attorney, Agent, or Firm* — Knobbe, Martens, Olson & Bear LLP

(57) ABSTRACT

The present invention relates generally to nucleic acid molecules in respect of which changes to DNA methylation levels are indicative of the onset or predisposition to the onset of a neoplasm. More particularly, the present invention is directed to nucleic acid molecules in respect of which changes to DNA methylation levels are indicative of the onset and/or progression of a large intestine or breast neoplasm, such as an adenoma or adenocarcinoma. The DNA methylation status of the present invention is useful in a range of applications including, but not limited to, those relating to the diagnosis and/or monitoring of colorectal or breast neoplasms, such as colorectal or breast adenocarcinomas. Accordingly, in a related aspect the present invention is directed to a method of screening for the onset, predisposition to the onset and/or progression of a neoplasm by screening for modulation in DNA methylation of one or more nucleic acid molecules. The nucleic acid molecules used for diagnostics in the present invention are sequences from LOC 100526820, subsequently named CAHM (colorectal adenocarcinoma hypermethylated).

9 Claims, 3 Drawing Sheets
Specification includes a Sequence Listing.

(56) References Cited

OTHER PUBLICATIONS

Altschul, Stephen F. et al., "Gapped BLAST and PSI-BLAST: a new generation of protein database search programs" Nucleic Acids Research, 1997, pp. 3389-3402, vol. 25, No. 17.
Ammerpohl, Ole et al., "Hunting for the 5th base: Techniques for analyzing DNA methylation" Biochim et Biophysica Acta, 2009, pp. 847-862, vol. 1790.
Beaucage, S. L. et al., "Deoxynucleoside Phosphoramidites—A New Class of Key Intermediates for Deoxypolynucleotide Synthesis" Tetrahedron Letters, 1981, pp. 1859-1862, vol. 22, No. 20.
Belousov, Evgeniy S. et al., "Sequence-specific targeting and covalent modification of human genomic DNA" Nucleic Acids Research, 1997, pp. 3440-3444, vol. 25, No. 17.
Blommers, M. J. J. et al., "Effects of the Introduction of L-Nucleotides in to DNA. Solution Structure of the Heterochiral Duplex d(G-C-G-(L)T-G-C-G)•d(C-G-C-A-C-G-C) Studied by NMR Spectroscopy" Biochemistry, 1994, pp. 7886-7896, vol. 33, No. 25.
Bonner, William M. et al., "A Film Detection Method for Tritium-Labelled Proteins and Nucleic Acids in Polyacrylamide Gels" Eur. J. Biocehm., 1974, pp. 83-88, vol. 46.
Breslauer, Kenneth J. et al., "Predicting DNA duplex stability from the base sequence" Proc. Natl. Acad. Sci. USA, Jun. 1986, pp. 3746-3750, vol. 83.
Brown, Eugene L. et al., "Chemical Synthesis and Cloning of a Tyrosine tRNA Gene" Methods in Enzymology, 1979, pp. 109-151, vol. 68.
Caruthers, M.H. et al., "Chemical Synthesis of Deoxyoligonucleotides by the Phosphoramidite Method" Methods in Enzymology, 1988, pp. 287-314, vol. 154.
Chen, Xiangning et al., "Template-directed dye-terminator incorporation (TDI) assay: a homogeneous DNA diagnostic method based on fluorescence resonance energy transfer" Nucleic Acids Research, 1997, pp. 347-353, vol. 25, No. 2.
Clark, Susan J. et al., "DNA methylation: Bisulphite modification and analysis" Nature Protocols, 2006, pp. 2353-2364, vol. 1, No. 5.
Cottrell, Susan E. et al., "A real-time PCR assay for DNA-methylation using methylation-specific blockers" Nucleic Acids Research, 2004, pp. 1-8, vol. 32, No. 1, e10.
Das, Partha M. et al., "DNA Methylation and Cancer" Journal of Clinical Oncology, Nov. 15, 2004, pp. 4632-4642, vol. 22, No. 22.
Degraves, Fred J. et al., "High-Sensitivity Quantitative PCT Platform" Biotechniques, 2003, pp. 106-115, vol. 34, No. 1.
Deiman, Birgit et al., "Characteristics and Applications of Nucleic Acid Sequence-Based Amplification (NASBA)" Molecular Biotechnology, 2002, pp. 163-179, vol. 20.
Deng, Da-Jun et al., "Detection of CPG Methylations in Human Mismatch Repair Gene HMLH1 Promoter by Denaturing High-Performance Liquid Chromatography (DHPLC)" Chinese Journal of Cancer Research, 2000, pp. 171&191, vol. 12, No. 3.
Devos, Theo et al., "Circulating Methylated SEPT9 DNA in Plasma Is a Biomarker for Colorectal Cancer" Clinical Chemistry, 2009, pp. 1337-1346, vol. 55, No. 7.
Eads, Cindy A. et al., "CpG Island Hypermethylation in Human Colorectal Tumors Is Not Associated with DNA Methyltransferase Overexpression" Cancer Research, May 15, 1999, pp. 2302-2306, vol. 59.
Egholm, Michael et al., "Peptide Nucleic Acids (PNA) Oligonucleotide Analogues with an Achiral Peptide Backbone" J. Am. Chem. Soc., 1992, pp. 1895-1897, vol. 114.
Egholm, Michael et al., "PNA hybridizes to complementary oligonucleotides obeying the Watson-Crick hydrogen-bonding rules" Nature, Oct. 7, 1993, pp. 566-568, vol. 365.
Frenkel, Krystyna et al., "7,12-Dimethylbenz[a]anthracene Induces Oxidative DNA Modification in Vivo" Free Radical Biology & Medicine, 1995, pp. 373-380, vol. 19, No. 3.
Frommer, Marianne et al., "A genomic sequencing protocol that yields a positive display of 5-methylcytosine residues in individual DNA strands" Proc. Natl. Acad. Sci. USA, Mar. 1992, pp. 1827-1831, vol. 89.

Gibson, Ursula E.M. et al., "A Novel Method for Real Time Quantitative RT-PCT" Genome Research, 1996, pp. 995-1001, vol. 6.
Golub, T. R. et al., "Molecular Classification of Cancer: Class Discovery and Class Prediction by Gene Expression Monitoring" Science, Oct. 15, 1999, pp. 531-537, vol. 286.
Gonzalgo, Mark L. et al., "Rapid quantitation of methylation differences at specific sites using methylation-sensitive single nucleotide primer extension (Ms-SNuPE)" Nucleic Acids Research, 1997 pp. 2529-2531, vol. 25, No. 12.
Gonzalgo, Mark L. et al., "Identification and Characterization of Differentially Methylated Regions of Genomic DNA by Methylation-sensitive Arbitrarily Primed PCR" Cancer Research, Feb. 15, 1997, pp. 594-599, vol. 57.
Herman, James G. et al., "Methylation-specific PCR: A novel PCR assay for methylation status of CpG islands" Proc. Natl. Acad. Sci. USA, Sep. 1996, pp. 9821-9826, vol. 93.
Holland, Pamela M. et al., "Detection of specific polymerase chain reaction product by utilizing the 5'→3' exonuclease activity of Thermus aquaticus DNA polymerase" Proc. Natl. Acad. Sci. USA, Aug. 1991, pp. 7276-7280, vol. 88.
Kawai, Jun et al., "Comparison of DNA Methylation Patterns among Mouse Cell Lines by Restriction Landmark Genomic Scanning" Molecular and Cellular Biology, Nov. 1994, pp. 7421-7427, vol. 14, No. 11.
Kibriya, Muhammad G. et al., "A genome-wide DNA methylation study in colorectal carcinoma" BMC Medical Genomics, 2011, pp. 1-16, vol. 4, No. 50.
Kristensen, Lasse Sommer et al., "PCR-Based Methods for Detecting Single-Locus DNA Methylation Biomarkers in Cancer Diagnostics, Prognostics, and Response to Treatment" Chemical Chemistry, 2009, pp. 1471-1483, vol. 55, No. 8.
Kuppuswamy, Mohan N. et al., "Single nucleotide primer extension to detect genetic diseases: Experimental application to hemophilia B (factor IX) and cystic fibrosis genes" Proc. Natl. Acad. Sci. USA, Feb. 1991, pp. 1143-1147, vol. 88.
Landegren, Ulf et al., "Reading Bits of Genetic Information: Methods for Single-Nucleotide Polymorphism Analysis" Genome Research, 1998, pp. 796-776, vol. 8.
Lee, Linda G. et al., "Allelic discrimination by nick-translation PCR with fluorogenic probes" Nucleic Acids Research, 1993, pp. 3761-3766, vol. 21, No. 16.
Markowitz, Sanford D. et al., "Molecular Basis of Colorectal Cancer" New England Journal of Medicine, 2009, pp. 2449-2460, vol. 361.
Marmur, J. et al., "Determination of the Base Composition of Deoxyribonucleic Acid from its Thermal Denaturation Temperature" J. Mol. Biol., 1962, pp. 109-118, vol. 5.
Mata, John E. et al., "A Hexameric Phosphorothioate Oligonucleotide Telomerase Inhibitor Arrests Growth of Burkitt's Lymphoma Cells in Vitro and in Vivo" Toxicology and Applied Pharmacology, 1997, pp. 189-197, vol. 144.
Messing, Joachim "New M13 Vectors for Cloning" Methods in Enzymology, 1983, pp. 20-78, vol. 101.
Mhlanga, Musa M. et al., "Using Molecular Beacons to Detect Single-Nucleotide Polymorphisms with Real-Time PCR" Methods, 2001, pp. 463-471, vol. 25.
Mori, Yuriko et al., "Novel Candidate Colorectal Cancer Biomarkers Identified by Methylation-Microarray-Based Scanning" Endocrine Related Cancer, Aug. 2011, pp. 465-478, vol. 18, No. 4.
Narang, S. A. et al., "Improved Phosphotriester Method for the Synthesis of Gene Fragments" Methods in Enzymology, 1979, pp. 90-98, vol. 68.
Nielsen, Poul et al., "Synthesis of 2'-O,3'-C-linked bicyclic nucleosides and bicyclic oligonucleotides" J. Chem. Soc., 1997, pp. 3423-3433, vol. 1.
Olek, Alexander et al., "The pre-implantation ontogeny of the H19 methylation imprint" Nature Genetics, Nov. 1997, pp. 275-276, vol. 17.
Ørum, Henrik et al., "Detection of the Factor V Leiden Mutation by Direct Allele-specific Hybridization of PCR Amplicons to Photoimmobilized Locked Nucleic Acids" Clinical Chemistry, 1999, pp. 1898-1905, vol. 45, No. 11.

(56) References Cited

OTHER PUBLICATIONS

Ørum, Henrik et al., "Single base pair mutation analysis by PNA directed PCR clamping" Nucleic Acids Research, 1993, pp. 5332-5336, vol. 21, No. 23.
Pedersen, Susanne K. et al., "Discovery and Validation of a Novel DNA Methylation Biomarker for Colorectal Cancer With Application to Blood Testing" Gastroenterology, May 2012, p. S-33, vol. 142, Issue 5, Supplement 1.
Pedersen, Susanne K. et al., "CAHM, a long non-coding RNA gene hypermethylated in colorectal neoplasia" Epigenetics, Aug. 2014, pp. 1071-1082, vol. 9, No. 8.
Rand, Keith N. et al., "Headloop suppression PCR and its application to selective amplification of methylated DNA sequences" Nucleic Acids Research, 2005, pp. 1-11, vol. 33, No. 14, e127.
Rand, Keith N. et al., "Bisulphite Differential Denaturation PCR for Analysis of DNA Methylation" Epigenetics, 2006, pp. 94-100, vol. 1, Issue 2.
Rein, Theo et al., "Identifying 5-methylcytosine and related modifications in DNA genomes" Nucleic Acids Research, 1998, pp. 2255-2264, vol. 26, No. 10.
Robinson, Mark D. et al., "Protocol matters: which methylome are you actually studying?" Epigenomics, 2010, pp. 587-598, vol. 2, No. 4.
Sadri, Ramin et al., "Rapid analysis of DNA methylation using new restriction enzyme sites created by bisulfite modification" Nucleic Acids Research, 1996, pp. 5058-5059, vol. 24, No. 24.
Samstag, W. et al., "Synthesis and Properties of New Antisense Oligodeoxynucleotides Containing Benzylphosphonate Linkages" Antisense & Nucleic Acid Drug Development, 1996, pp. 153-156, vol. 6.
Santalucia, Jr., John "A unified view of polymer, dumbbell, and oligonucleotide DNA nearest-neighbor thermodynamics" Proc. Natl. Acad. Sci. USA, Feb. 1998, pp. 1460-1465, vol. 95.
Shames, David S. et al., "Methods for detecting DNA methylation in tumors: From bench to bedside" Cancer Letters, 2007, pp. 187-198, vol. 251.
Simeonov, Anton et al., "Single nucleotide polymorphism genotyping using short, fluorescently labeled locked nucleic acid (LNA) probes and fluorescence polarization detection" Nucleic Acids Research, 2002, pp. 1-5, vol. 30, No. 17, e91.
Singer-Sam, Judith et al., "A quantitative HpaII-PCR assay to measure methylation of DNA from a small number of cells" Nucleic Acids Research, 1990, p. 687, vol. 18, No. 3.
Singer-Sam, Judith et al., "A Sensitive, Quantitative Assay for Measurement of Allele-specific Transcripts Differing by a Single Nucleotide" Genome Res., 1992, pp. 160-163, vol. 1.
Singh, Sanjay K. et al., "Universality of LNA-mediated high-affinity nucleic acid recognition" Chem. Commun. 1998, pp. 1247-1248.
Southern, E.M. et al., "Analyzing and Comparing Nucleic Acid Sequences by Hybridization to Arrays of Oligonucleotides: Evaluation Using Experimental Models" Genomics, 1992, pp. 1008-1017, vol. 13.
Strauss-Soukup, J.K. et al., "Effects of Neutralization Pattern and Stereochemistry on DNA Bending by Methylphosphonate Substitutions" Biochemistry, 1997, pp. 8692-8698, vol. 36.
Szabo, Piroska E. et al., "Allele-specific expression and total expression levels of imprinted genes during early mouse development: implications for imprinting mechanisms" Genes & Development, 1995, pp. 3097-3108, vol. 9.
Toyota, Minoru et al., "Identification of Differentially Methylated Sequences in Colorectal Cancer by Methylated CpG Island Amplification" Cancer Research, May 15, 1999, pp. 2307-2312, vol. 59.
Uhlmann, Karen et al., "Evaluation of a potential epigenetic biomarker by quantitative methyl-single nucleotide polymorphism analysis" Electrophoresis, 2002, pp. 4072-4079, vol. 23.
Wedemeyer, Niels et al., "Flow Cytometric Quantification of Competitive Reverse Transcription—PCR Products" Clinical Chemistry, 2002, pp. 1398-1504, vol. 48, No. 9.
Weissleder, Ralph et al., "In vivo magnetic resonance imaging of transgene expression" Nature Medicine, Mar. 2000, pp. 351-354, vol. 6, No. 3.
Weitzel, Jeffrey N. "Genetic Cancer Risk Assessment—Putting It All Together" Cancer Supplement, Dec. 1, 1999, pp. 2483-2492, vol. 86, No. 11.
Xiong, Zhenggang et al., "COBRA: a sensitive and quantitative DNA methylation assay" Nucleic Acids Research, 1997, pp. 2532-2534, vol. 25, No. 12.
Yang, Guodong et al., "RNA-Binding Protein Quaking, a Critical Regulator of Colon Epithelial Differentiation and a Suppressor of Colon Cancer" Gastroenterology, 2010, pp. 231-240, vol. 138.
International Search Report for PCT/AU2012/000999 dated Sep. 20, 2012.
Bonaldo, Maria De Fatima et al., "Normalization and Subtraction: Two Approaches to Facilitate Gene Discovery" Genome Research, 1996, pp. 791-806, vol. 6.
Lofton-Day, Catherine et al., "DNA Methylation Biomarkers for Blood-Based Colorectal Cancer Screening" Clinical Chemistry, 2008, pp. 414-423, vol. 54, No. 2.
Mill, J., et al., Whole genome amplification of sodium bisulfite-treated DNA allows the accurate estimate of methylated cytosine density in limited DNA resources, BioTechniques 41:603-607, Nov. 2006.
Usadel, H., et al., Quantitative Adenomatous *Polyposis coli* Promoter Methylation Analysis in Tumor Tissue, Serum, and Plasma DNA of Patients with Lung Cancer, American Association for Cancer Research 62, 371-375, Jan. 15, 2002.

\* cited by examiner (a)

```
    163834295    ATCTGTAAAA ATGTTGACTT CTGCTTTTCA GACTACGCGC ACAGCCTCTT   163834344
Fig Ref position                                         ↑36
                                                         ↑38

TATTTCCTAC TGCGGCTTCA TTCCCTCACG GAACACTGAC GCCATCGCGA   163834394
                               ↑63         ↑79        ↑90      ↑96
                                                                ↑98

AGGAAGCATT TCGAGCACGA CTGACGCTCC CCTTATTATT TGCTAAGCCG   163834444
                             ↑112 ↑118   ↑125                        ↑149

'445       '455        '465       '475       '485
                 CTGCGCTCGG GTCTGGCTAC GATTTGCTTT CAGAATAACG GGAAGGTGCA   163834494
                 ↑154↑158               ↑170                  ↑189

ACAAG       163834500
```

```
163834621   GCCGTGCTGC TTTCCAGCCT CTCAGCAAAT CACCAACACC GAAAGAAGCC   163834670
                                            ↑33    ↑40

ACGGCGGCGA CGGGAGGGGC GTCGCGCGTG CTTCCCTCGG CGACAAAGCG   163834720
            ↑52↑55↑58 ↑60       ↑70 ↑75

GGAGCCGGGC GCGCCGGCCG AGGGCGCCCG GCGCAGAGTC CCGCAGAGGC   163834770
                                              ↑132              ↑150

GGACGCCGCG GCACGCGCCT CGAAAAGCCT CAAACTCTTA TCCTCGGCTC   163834820
                                  ↑171                        ↑194

TCCCGCCCCA CCTCCGCCCC GCAGCCAAGA CCCGCGCCGT GGCGGGCCCG   163834870
            ↑204      ↑215 ↑220               ↑233 ↑238 ↑243 ↑249

ACGGCCAAGG AAAGCCCACC AGCCCTCCGC ACCGTG   163834906
            ↑252
```

(b)

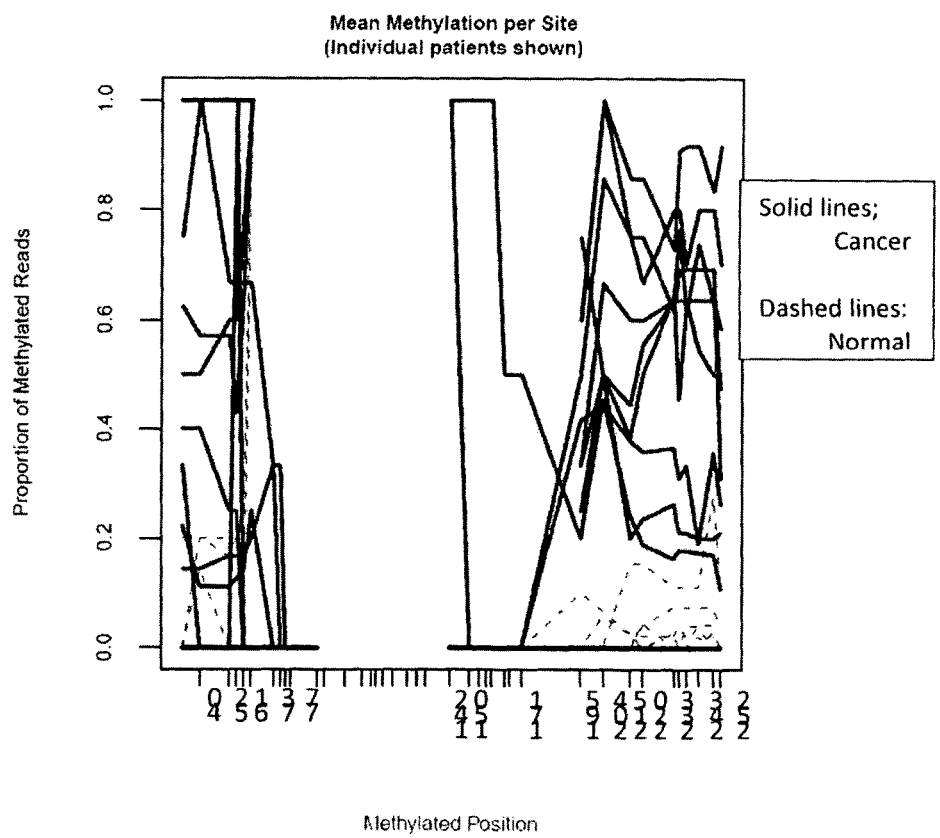

FIGURE 3

SEQ ID NO:1

| | | | | | |
|---|---|---|---|---|---|
| 163834295 | ATCTGTAAAA ATGTTGACTT CTGCTTTTCA GACTACGCGC ACAGCCTCTT | 163834344 |
| | TATTTCCTAC TGCGGCTTCA TTCCCTCACG GAACACTGAC GCCATCGCGA | 163834394 |
| | AGGAAGCATT TCGAGCACGA CTGACGCTCC CCTTATTATT TGCTAAGCCG | 163834444 |
| | CTGCGCTCGG GTCTGGCTAC GATTTGCTTT CAGAATAACG GGAAGGTGCA | 163834494 |
| | ACAAGA | 163834500 |

SEQ ID NO:2

| | | | | | |
|---|---|---|---|---|---|
| 163834621 | GCCGTGCTGC TTTCCAGCCT CTCAGCAAAT CACGAACACC GAAAGAAGCC | 163834670 |
| | ACGGCGGCGA CGGGAGGGGC GTCGCGCGTG CTTCCCTCGG CGACAAAGCG | 163834720 |
| | GGAGCCGGGC GCGCCGGCCG AGGGCGCCCG GCGCAGAGTC CCGCAGAGGC | 163834770 |
| | GGACGCCGCG GCACGCGCCT CGAAAAGCCT CAAACTCTTA TCCTCGGCTC | 163834820 |
| | TCCCGCCCCA CCTCCGCCCC GCAGCCAAGA CCCGCGCCGT GGCGGGCCCG | 163834870 |
| | ACGGCCAAGG AAAGCCCACC AGCCCTCCGC ACCGTG | 163834906 |

SEQUENCE LISTING

```
<160> NUMBER OF SEQ ID NOS: 25

<210> SEQ ID NO 1
<211> LENGTH: 206
<212> TYPE: DNA
<213> ORGANISM: homo sapien

<400> SEQUENCE: 1
atctgtaaaa atgttgactt ctgcttttca gactacgcgc acagcctctt tatttcctac      60
tgcggcttca ttccctcacg gaacactgac gccatcgcga aggaagcatt tcgagcacga     120
ctgacgctcc ccttattatt tgctaagccg ctgcgctcgg gtctggctac gatttgcttt     180
cagaataacg ggaaggtgca acaaga                                          206
```

<210> SEQ ID NO 2
<211> LENGTH: 286
<212> TYPE: DNA
<213> ORGANISM: homo sapien

<400> SEQUENCE: 2

| | | | | | |
|---|---|---|---|---|---|
| gccgtgctgc | tttccagcct | ctcagcaaat | cacgaacacc | gaaagaagcc | acggcggcga | 60 |
| cgggaggggc | gtcgcgcgtg | cttccctcgg | cgacaaagcg | ggagccgggc | gcgccggccg | 120 |
| agggcgcccg | gcgcagagtc | ccgcagaggc | ggacgccgcg | gcacgcgcct | cgaaaagcct | 180 |
| caaactctta | tcctcggctc | tcccgcccca | cctccgcccc | gcagccaaga | cccgcgccgt | 240 |
| ggcgggcccg | acggccaagg | aaagcccacc | agccctccgc | accgtg | | 286 |

<210> SEQ ID NO 3
<211> LENGTH: 63
<212> TYPE: DNA
<213> ORGANISM: homo sapien

<400> SEQUENCE: 3

| | | | | | |
|---|---|---|---|---|---|
| gaaggaagca | tttcgagcac | gactgacgct | ccccttatta | tttgctaagc | cgctgcgctc | 60 |
| ggg | | | | | | 63 |

<210> SEQ ID NO 4
<211> LENGTH: 127
<212> TYPE: DNA
<213> ORGANISM: homo sapien

<400> SEQUENCE: 4

| | | | | | |
|---|---|---|---|---|---|
| gaaggaagca | tttcgagcac | gactgacgct | ccccttatta | tttgctaagc | cgctgcgctc | 60 |
| gggtctggct | acgatttgct | ttcagaataa | cgggaaggtg | caacaagatc | gcttccctag | 120 |
| aggcgcg | | | | | | 127 |

<210> SEQ ID NO 5
<211> LENGTH: 206
<212> TYPE: DNA
<213> ORGANISM: homo sapien

<400> SEQUENCE: 5

| | | | | | |
|---|---|---|---|---|---|
| atttgtaaaa | atgttgattt | tgttttttta | gattatgtgt | atagttttt | tatttttat | 60 |
| tgtggtttta | tttttttatg | gaatattgat | gttattgtga | aggaagtatt | tgagtatga | 120 |
| ttgatgtttt | tttattatt | tgttaagttg | ttgtgtttgg | gtttggttat | gatttgtttt | 180 |
| tagaataatg | ggaaggtgta | ataaga | | | | 206 |

<210> SEQ ID NO 6
<211> LENGTH: 206
<212> TYPE: DNA
<213> ORGANISM: homo sapien

<400> SEQUENCE: 6

| | | | | | |
|---|---|---|---|---|---|
| atttgtaaaa | atgttgattt | tgttttttta | gattacgcgt | atagttttt | tatttttat | 60 |
| tgcggtttta | tttttttacg | gaatattgac | gttatcgcga | aggaagtatt | tcgagtacga | 120 |
| ttgacgtttt | tttattatt | tgttaagtcg | ttgcgttcgg | gtttggttac | gatttgtttt | 180 |
| tagaataacg | ggaaggtgta | ataaga | | | | 206 |

```
<210> SEQ ID NO 7
<211> LENGTH: 286
<212> TYPE: DNA
<213> ORGANISM: homo sapien

<400> SEQUENCE: 7
gttgtgttgt ttttagttt ttagtaaat tatgaatatt gaaagaagtt atggtggtga      60
tgggaggggt gttgtgtgtg ttttttttgg tgataaagtg ggagttgggt gtgttggttg     120
agggtgtttg gtgtagagtt ttgtagaggt ggatgttgtg gtatgtgttt tgaaaagttt    180
taaattttta ttttttggttt ttttgttta ttttttgtttt gtagttaaga tttgtgttgt    240
ggtgggtttg atggttaagg aaagtttatt agttttttgt attgtg                   286

<210> SEQ ID NO 8
<211> LENGTH: 286
<212> TYPE: DNA
<213> ORGANISM: homo sapien

<400> SEQUENCE: 8
gtcgtgttgt ttttagttt ttagtaaat tacgaatatc gaaagaagtt acggcggcga      60
cgggaggggc gtcgcgcgtg ttttttttcgg cgataaagcg ggagtcgggc gcgtcggtcg    120
agggcgttcg gcgtagagtt tcgtagaggt ggacgtcgcg gtacgcgttt cgaaaagttt    180
taaattttta ttttcggttt tttcgtttta ttttcgtttc gtagttaaga ttcgcgtcgt    240
ggcgggttcg acggttaagg aaagtttatt agttttttcgt atcgtg                  286

<210> SEQ ID NO 9
<211> LENGTH: 63
<212> TYPE: DNA
<213> ORGANISM: homo sapien

<400> SEQUENCE: 9
gaaggaagta ttttgagtat gattgatgtt ttttttatta tttgttaagt tgttgtgttt     60
ggg                                                                  63

<210> SEQ ID NO 10
<211> LENGTH: 63
<212> TYPE: DNA
<213> ORGANISM: homo sapien

<400> SEQUENCE: 10
gaaggaagta ttcgagtac gattgacgtt ttttttatta tttgttaagt cgttgcgttc     60
ggg                                                                  63

<210> SEQ ID NO 11
<211> LENGTH: 127
<212> TYPE: DNA
<213> ORGANISM: homo sapien

<400> SEQUENCE: 11
gaaggaagta ttttgagtat gattgatgtt ttttttatta tttgttaagt tgttgtgttt     60
gggtttggtt atgatttgtt tttagaataa tgggaaggtg taataagatt gttttttttag   120 aggtgtg                                                              127

<210> SEQ ID NO 12
<211> LENGTH: 127
<212> TYPE: DNA
```

```
<400> SEQUENCE: 12
gaaggaagta tttcgagtac gattgacgtt ttttttatta tttgttaagt cgttgcgttc    60
gggtttggtt acgatttgtt tttagaataa cgggaaggtg taataagatc gttttttttag   120 aggcgcg                                                              127

<210> SEQ ID NO 13
<211> LENGTH: 27
<212> TYPE: DNA
<213> ORGANISM: homo sapien

<400> SEQUENCE: 13
gaaggaagta tttcgagtac gattgac                                         27

<210> SEQ ID NO 14
<211> LENGTH: 19
<212> TYPE: DNA
<213> ORGANISM: homo sapien

<400> SEQUENCE: 14
cccgaacgca acgacttaa                                                  19

<210> SEQ ID NO 15
<211> LENGTH: 28
<212> TYPE: DNA
<213> ORGANISM: homo sapien

<400> SEQUENCE: 15
gcctctaaaa aaacgatctt attacacc                                        28

<210> SEQ ID NO 16
<211> LENGTH: 1535
<212> TYPE: DNA
<213> ORGANISM: homo sapien

<400> SEQUENCE: 16
ccccggagcg cgcctgcgtg gggcgggggc ggcagccgac tagggctgg gtctggccgt      60 ttagggccgg gtcttggccc gtcgcccacg gtgcggaggg ctggtgggct tccttggcc    120 gtcgggcccg ccacggcgcg ggtcttggct gcggggcgga ggtggggcgg gagagccgag   180
gataagagtt tgaggctttt cgaggcgcgt gccgcgcgt ccgcctctgc gggactctgc    240
gccgggcgcc ctcggccggc gcgcccggct cccgctttgt cgccgaggga agcacgcgcg   300
acgcccctcc cgtcgccgcc gtggcttctt tcggtgttcg tgatttgctg agaggctgga   360
aagcagcacg gcggagagga gccttgcact cgccaggcgg gaagcctgcg cggacacgcg   420
tgcgcaccca cggggcggcg ggcggccgtg ggggtccgg gccacgcggg cgacgcgcct    480
ctagggaagc gatcttgttg caccttcccg ttattctgaa agcaaatcgt agccagaccc   540
gagcgcagcg gcttagcaaa taataagggg agcgtcagtc gtgctcgaaa tgcttccttc   600
gcgatggcgt cagtgttccg tgagggaatg aagccgcagt aggaaataaa gaggctgtgc   660
gcgtagtctg aaaagcagaa gtcaacattt ttacagatga agaaagaata cggaggcaag   720
aggtctttct ctgcagtttg gtggatttcc aacatttaga cttgtttgga agaatttcct   780
cagctgcacc aatgaagtcc ttgatctata gaagtcggca gtccctaaat ctacgtctgc   840
attttgttgc aaatccttta taacattcca ttaaaataat gcagagttat ttaatatcca   900
gttggccatc gtgagagtaa ttcgcggctg agatttgtt aatcattctg tcttctgact   960
taacagtgaa cgtaggtgat tttttttgta aaatgttgct tcacatgaat tgtgagaatc  1020
```

```
acctctaagt ttgaattgta ctgaaggcac tataagaatt tcaaatgaac gctgagtagc    1080
cagtagcctt ctggcctttt cgttaacaa gcacagagtt cgtttttaaa attaagttac    1140
tttgacagag gaaatgtaat agccttggta gacaacatta aaaatgtaac tgtcagatgt    1200
tttaaagtct ccaacagccg tatctgtttt agagccatag aatatttact tactgaattg    1260 cctgttaaa gatgaacttt ctaaatgcag ggaatagtaa cttgcaaaaa agctatggtc    1320
tctaagtaat gaaggctgtt tcagtaccta gaaaaatcaa atcaaggtt ttgatgctgc    1380 tagtgtaaaa gatgcaatcc ccttcttaat ggcctgctta tttattaagc tcctaggcac    1440
tatgctgaat gccctacatg catatctcgt ttaatcatca gtacaacttg ggcttaggtt    1500
agactgttat ccccatttta caaataaggg gaaac                              1535

<210> SEQ ID NO 17
<211> LENGTH: 886
<212> TYPE: DNA
<213> ORGANISM: homo sapien

<400> SEQUENCE: 17
cgcctgcgtg gggcggggc ggcagccgac taggggctgg gtctggccgt ttagggccgg      60
gtcttggccc gtcgcccacg gtgcggaggg ctggtgggct ttccttggcc gtcgggcccg    120
ccacggcgcg ggtcttggct cggggcgga ggtggggcgg gagagccgag gataagagtt    180 tgaggcttt cgaggcgcgt gccgcggcgt ccgcctctgc gggactctgc gccgggcgcc    240
ctcggccggc gcgcccggct cccgctttgt cgccgaggga agcacgcgcg acgcccctcc    300
cgtcgccgcc gtggcttctt tcggtgttcg tgatttgctg agaggctgga aagcagcacg    360
gcggagagga gccttgcact cgccaggcgg gaagcctgcg cggacacgcg tgcgcaccca    420
cggggcggcg ggcgggcgtg gggggtccgg gccacgcggg cgacgcgcct ctagggaagc    480
gatcttgttg caccttcccg ttattctgaa agcaaatcgt agccagaccc gagcgcagcg    540
gcttagcaaa taataagggg agcgtcagtc gtgctcgaaa tgcttccttc gcgatggcgt    600
cagtgttccg tgagggaatg aagccgcagt aggaaataaa gaggctgtgc gcgtagtctg    660
aaaagcagaa gtcaacattt ttacagatga agaaagaata cggaggcaag aggtctttct    720
ctgcagtttg gtggatttcc aacatttaga cttgtttgga agaatttcct cagctgcacc    780
aatgaagtcc ttgatctata gaagtcggca gtccctaaat ctacgtctgc attttgttgc    840 aaatcctta taacattcca ttaaaataat gcagagttat ttaata               886

<210> SEQ ID NO 18
<211> LENGTH: 33
<212> TYPE: DNA
<213> ORGANISM: artificial
<220> FEATURE:
<223> OTHER INFORMATION: primer

<400> SEQUENCE: 18
atttgtaaaa atgttgattt ttgttttta gat                                   33

<210> SEQ ID NO 19
<211> LENGTH: 26
<212> TYPE: DNA
<213> ORGANISM: artificial
<220> FEATURE:
<223> OTHER INFORMATION: primer

<400> SEQUENCE: 19
tcttattaca ccttcccrtt attcta                                          26
```

```
<210> SEQ ID NO 20
<211> LENGTH: 31
<212> TYPE: DNA
<213> ORGANISM: artificial
<220> FEATURE:
<223> OTHER INFORMATION: primer

<400> SEQUENCE: 20
gtygtgttgt tttttagttt tttagtaaat t                               31

<210> SEQ ID NO 21
<211> LENGTH: 31
<212> TYPE: DNA
<213> ORGANISM: artificial
<220> FEATURE:
<223> OTHER INFORMATION: primer

<400> SEQUENCE: 21
cacratacra aaaactaata aactttcctt a                               31

<210> SEQ ID NO 22
<211> LENGTH: 25
<212> TYPE: DNA
<213> ORGANISM: Artificial
<220> FEATURE:
<223> OTHER INFORMATION: probe

<400> SEQUENCE: 22
atggatgaag aaagaaagga tgagt                                      25

<210> SEQ ID NO 23
<211> LENGTH: 24
<212> TYPE: DNA
<213> ORGANISM: Artificial
<220> FEATURE:
<223> OTHER INFORMATION: primer

<400> SEQUENCE: 23
gtgatggagg aggtttagta agtt                                       24

<210> SEQ ID NO 24
<211> LENGTH: 26
<212> TYPE: DNA
<213> ORGANISM: Artificial
<220> FEATURE:
<223> OTHER INFORMATION: primer

<400> SEQUENCE: 24
aattacaaaa accacaacct aataaa                                     26

<210> SEQ ID NO 25
<211> LENGTH: 30
<212> TYPE: DNA
<213> ORGANISM: Artificial
<220> FEATURE:
<223> OTHER INFORMATION: probe

<400> SEQUENCE: 25
accaccaccc aacacacaat aacaaacaca                                 30
```

DNA METHYLATION IN COLORECTAL AND BREAST CANCER DIAGNOSTIC METHODS

CROSS REFERENCE TO RELATED APPLICATIONS

This application is a U.S. National Phase Application of PCT International Application Number PCT/AU2012/000999, filed on Aug. 24, 2012, designating the United States of America and published in the English language, which is an International Application of and claims the benefit of priority to U.S. Provisional Application No. 61/527,503, filed on Aug. 25, 2011. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-WMRK4-004APC.txt, the date of creation of the ASCII text file is Feb. 24, 2014, and the size of the ASCII text file is 10 KB.

FIELD OF THE INVENTION

The present invention relates generally to nucleic acid molecules in respect of which changes to DNA methylation levels are indicative of the onset or predisposition to the onset of a neoplasm. More particularly, the present invention is directed to nucleic acid molecules in respect of which changes to DNA methylation levels are indicative of the onset and/or progression of a large intestine or breast neoplasm, such as an adenoma or adenocarcinoma. The DNA methylation status of the present invention is useful in a range of applications including, but not limited to, those relating to the diagnosis and/or monitoring of colorectal or breast neoplasms, such as colorectal or breast adenocarcinomas. Accordingly, in a related aspect the present invention is directed to a method of screening for the onset, predisposition to the onset and/or progression of a neoplasm by screening for modulation in DNA methylation of one or more nucleic-acid molecules.

BACKGROUND OF THE INVENTION

Colorectal cancer includes cancerous growths in the colon, rectum and appendix. With 655,000 deaths worldwide per year, it is the fourth most common form of cancer in the United States and the third leading cause of cancer-related death in the Western world. Colorectal cancers arise from adenomatous polyps in the colon. These mushroom-shaped growths are usually benign, but some develop into cancer over time. Localized colon cancer is usually diagnosed through colonoscopy. Invasive cancers that are confined within the wall of the colon (TNM stages I and II) are curable with surgery. If untreated, they spread to regional lymph nodes (stage III), where up to 73% are curable by surgery and chemotherapy. Cancer that metastasizes to distant sites (stage IV) is usually not curable, although chemotherapy can extend survival, and in rare cases, surgery and chemotherapy together have seen patients through to a cure (Markowitz and Bertagnolli, 2009, *N. Engl. J. Med.* 361(25): 2449-60). Radiation is used with rectal cancer.

Breast cancer is a type of cancer originating from breast tissue, most commonly from the inner lining of milk ducts or the lobules that supply the ducts with milk. Cancers originating from ducts are known as ductal carcinomas, while those originating from lobules are known as lobular carcinomas. While the overwhelming majority of cases occur in women, male breast cancer can also occur.

Worldwide, breast cancer comprises 22.9% of all cancers in women and is more than 100 times more common in women than in men, although men tend to have poorer outcomes due to delays in diagnosis. Prognosis and survival rates for breast cancer vary greatly depending on the cancer type, stage, treatment, and geographical location of the patient. Survival rates in the Western world are high; for example, more than 8 out of 10 women (84%) in England diagnosed with breast cancer survive for at least 5 years. In developing countries, however, survival rates are much poorer.

Many cancers are preceded by adenomas. Adenomas are benign tumours, or neoplasms, of epithelial origin which are derived from glandular tissue or exhibit clearly defined glandular structures. Some adenomas show recognisable tissue elements, such as fibrous tissue (fibroadenomas) and epithelial structure, while others, such as bronchial adenomas, produce active compounds that might give rise to clinical syndromes.

Adenomas may progress to become an invasive neoplasm and are then termed adenocarcinomas. Accordingly, adenocarcinomas are defined as malignant epithelial tumours arising from glandular structures, which are constituent parts of many organs of the body. The term adenocarcinoma is also applied to tumours showing a glandular growth pattern. These tumours may be sub-classified according to the substances that they produce, for example mucus secreting and serous adenocarcinomas, or to the microscopic arrangement of their cells into patterns, for example papillary and follicular adenocarcinomas. These carcinomas may be solid or cystic (cystadenocarcinomas). Each organ may produce tumours showing a variety of histological types, for example the ovary may produce both mucinous and cystadenocarcinoma.

Adenomas in different organs behave differently. In general, the overall chance of carcinoma being present within an adenoma (i.e. a focus of cancer having developed within a benign lesion) is approximately 5%. However, this is related to size of an adenoma. For instance, in the large bowel (colon and rectum specifically) occurrence of a cancer within an adenoma is rare in adenomas of less than 1 centimeter. Such a development is estimated at 40 to 50% in adenomas which are greater than 4 centimeters and show certain histopathological change such as villous change, or high grade dysplasia. Adenomas with higher degrees of dysplasia have a higher incidence of carcinoma. In any given colorectal adenoma, the predictors of the presence of cancer now or the future occurrence of cancer in the organ include size (especially greater than 9 mm) degree of change from tubular to villous morphology, presence of high grade dysplasia and the morphological change described as "serrated adenoma". In any given individual, the additional features of increasing age, familial occurrence of colorectal adenoma or cancer, male gender or multiplicity of adenomas, predict a future increased risk for cancer in the organ—so-called risk factors for cancer. Except for the presence of adenomas and its size, none of these is objectively defined and all those other than number and size are subject to observer error and to confusion as to precise definition of the feature in question. Because such factors can be difficult to assess and define, their value as predictors of current or future risk for cancer is imprecise.

Once a sporadic adenoma has developed, the chance of a new adenoma occurring is approximately 30% within 26 months.

The symptoms of colorectal cancer depend on the location of tumor in the bowel, and whether is has metastasised. Unfortunately, many of the symptoms may occur in other diseases as well, and hence symptoms may not be conclusively diagnostic of colorectal cancer.

Local symptoms are more likely if the tumor is located closer to the anus. There may be a change in bowel habit (new-onset constipation or diarrhea in the absence of another cause), a feeling of incomplete defecation and reduction in diameter of stools. Tenesmus and change in stool shape are both characteristic of rectal cancer. Lower gastrointestinal bleeding, including the passage of bright red blood in the stool, may indicate colorectal cancer, as may the increased presence of mucus. Melena, black stool with a tarry appearance, normally occurs in upper gastrointestinal bleeding (such as from a duodenal ulcer), but is sometimes encountered in colorectal cancer when the disease is located in the beginning of the large bowl.

A tumor that is large enough to fill the entire lumen of the bowel may cause bowel obstruction. This situation is characterized by constipation, abdominal pain, abdominal distension and vomiting. This occasionally leads to the obstructed and distended bowel perforating and causing peritonitis.

Certain local effects of colorectal cancer occur when the disease has become more advanced. A large tumor is more likely to be noticed on feeling the abdomen, and it may be noticed by a doctor on physical examination. The disease may invade other organs, and may cause blood or air in the urine or vaginal discharge.

If a tumor has caused chronic occult bleeding, iron deficiency anaemia may occur. This may be experienced as fatigue, palpitations and noticed as pallor. Colorectal cancer may also lead to weight loss, generally due to a decreased appetite.

More unusual constitutional symptoms are an unexplained fever and one of several paraneoplastic syndromes. The most common paraneoplastic syndrome is thrombosis, usually deep vein thrombosis.

Colorectal cancer most commonly spreads to the liver. This may go unnoticed, but large deposits in the liver may cause jaundice and abdominal pain (due to stretching of the capsule). If the tumor deposit obstructs the bile duct, the jaundice may be accompanied by other features of biliary obstruction, such as pale stools.

Colorectal cancer can take many years to develop and early detection of colorectal cancer greatly improves the prognosis. Even modest efforts to implement colorectal cancer screening methods can result in a drop in cancer deaths. Despite this, colorectal cancer screening rates remain low. Therefore, screening for the disease is recommended in individuals who are at increased risk. There are currently several different tests available for this purpose:

Digital rectal exam: The doctor inserts a lubricated, gloved finger into the rectum to feel for abnormal areas. It only detects tumors large enough to be felt in the distal part of the rectum but is useful as an initial screening test.

Faecal occult blood test: a test for blood in the stool. Two types of tests can be used for detecting occult blood in stools i.e. guaiac based (chemical test) and immunochemical. The sensitivity of immunochemical testing is superior to that of chemical testing without an unacceptable reduction in specificity (Weitzel J N (December 1999). "Genetic cancer risk assessment. Putting it all together". *Cancer* 86 (11 Suppl): 2483-92).

Endoscopy:
Sigmoidoscopy: A lit probe (sigmoidoscope) is inserted into the rectum and lower colon to check for polyps and other abnormalities.

Colonoscopy: A lit probe called a colonoscope is inserted into the rectum and the entire colon to look for polyps and other abnormalities that may be caused by cancer. A colonoscopy has the advantage that if polyps are found during the procedure they can be removed immediately. Tissue can also be taken for biopsy.

Double contrast barium enema (DCBE): First, an overnight preparation is taken to cleanse the colon. An enema containing barium sulfate is administered, then air is insufflated into the colon, distending it. The result is a thin layer of barium over the inner lining of the colon which is visible on X-ray films. A cancer or a precancerous polyp can be detected this way. This technique can miss the (less common) flat polyp.

Virtual colonoscopy replaces X-ray films in the double contrast barium enema (above) with a special computed tomography scan and requires special workstation software in order for the radiologist to interpret. This technique is approaching colonoscopy in sensitivity for polyps. However, any polyps found must still be removed by standard colonoscopy.

Standard computed axial tomography is an x-ray method that can be used to determine the degree of spread of cancer, but is not sensitive enough to use for screening. Some cancers are found in CAT scans performed for other reasons.

Blood tests: Measurement of the patient's blood for elevated levels of certain proteins can give an indication of tumor load. In particular, high levels of carcinoembryonic antigen (CEA) in the blood can indicate metastasis of adenocarcinoma. These tests are frequently false positive or false negative, and are not recommended for screening, it can be useful to assess disease recurrence. CA 19-9 and CA 242 biomarkers can indicate e-selectin related metastatic risks, help follow therapeutic progress, and assess disease recurrence. Recently, an assay for detection in plasma of methylated sequences of the Septin 9 gene has also become available to assist in diagnosis of colorectal cancer.

Positron emission tomography (PET) is a 3-dimensional scanning technology where a radioactive sugar is injected into the patient, the sugar collects in tissues with high metabolic activity, and an image is formed by measuring the emission of radiation from the sugar. Because cancer cells often have very high metabolic rates, this can be used to differentiate benign and malignant tumors. PET is not used for screening and does not (yet) have a place in routine workup of colorectal cancer cases.

Whole-body PET imaging is the most accurate diagnostic test for detection of recurrent colorectal cancer, and is a cost-effective way to differentiate resectable from nonresectable disease. A PET scan is indicated whenever a major management decision depends upon accurate evaluation of tumour presence and extent.

Stool DNA testing is an emerging technology in screening for colorectal cancer. Premalignant adenomas and cancers shed DNA markers from their cells which are not degraded during the digestive process and remain stable in the stool. Capture, followed by PCR amplifies the DNA to detectable levels for assay.

High C-Reactive Protein levels as risk marker (http://www.sciencedaily.com/releases/2010/04/100419150831.htm).

Despite the existence of these tests, diagnosis remains problematic. Most of the more sensitive tests are quite invasive and expensive and therefore uptake by patients is low. There is therefore an ongoing need to develop simpler and more informative diagnostic protocols or aids to diagnosis that enable one to direct colonoscopy at people more likely to have developed adenomas or carcinomas. A simple and accurate screening test would enable much more widely applicable screening systems to be set up. Similarly, with breast cancer there is a significantly better prognosis if the cancer is diagnosed early, this often being difficult to reliably achieve since other than the BRCA gene test as a prognostic indicator of a sub-group of aggressive cancers, reliance still lies primarily with mammograms and self examination to identify tumours, neither technique of which is sensitive enough to reliably detect very early stage cancers.

In work leading up to the present invention it has been determined that changes to the methylation of LOC100526820, in particular two specific regions of LOC100526820, is indicative of the development of neoplasms of the large intestine, such as adenomas and adenocarcinomas. Still further, the identification of specific genomic DNA cytosine nucleotides which become hypermethylated has enabled the development of very simple and specific amplification reactions for routine use in the context of diagnosis.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains nucleotide sequence information prepared using the programme PatentIn Version 3.5, presented herein after the bibliography. Each nucleotide sequence is identified in the sequence listing by the numeric indicator <210> followed by the sequence identifier (eg. <210>1, <210>2, etc). The length, type of sequence (DNA, etc) and source organism for each sequence is indicated by information provided in the numeric indicator fields <211>, <212> and <213>, respectively. Nucleotide sequences referred to in the specification are identified by the indicator SEQ ID NO: followed by the sequence identifier (eg. SEQ ID NO:1, SEQ ID NO:2, etc.). The sequence identifier referred to in the specification correlates to the information provided in numeric indicator field <400> in the sequence listing, which is followed by the sequence identifier (eg. <400>1, <400>2, etc). That is SEQ ID NO:1 as detailed in the specification correlates to the sequence indicated as <400>1 in the sequence listing.

One aspect of the present invention is directed to a method of screening for the onset or predisposition to the onset of a large intestine or breast neoplasm in an individual, said method comprising assessing the methylation status of the DNA region defined by Hg19 coordinates Chr6: 163834097-163834982 in a biological sample from said individual wherein a higher level of methylation of said DNA region relative to control levels is indicative of a neoplastic large intestine or breast cell or a cell predisposed to the onset of a neoplastic state.

In another aspect there is provided a method of screening for the onset or predisposition to the onset of a large intestine or breast neoplasm in a human, said method comprising assessing the methylation status of the DNA region defined by Hg19 coordinates Chr6: 163834097-163834982 in a biological sample from said individual wherein a higher level of methylation of said DNA region relative to control levels is indicative of a neoplastic large intestine or breast cell or a cell predisposed to the onset of a neoplastic state.

Yet another aspect of the present invention is directed to a method of screening for the onset or predisposition to the onset of a large intestine or breast neoplasm in an individual, said method comprising assessing the methylation status of a DNA region selected from one or both of the regions defined by Hg19 coordinates Chr6:163834295-163834500 or Chr6:163834621-163834906 in a biological sample from said individual wherein a higher level of methylation of one or both of these DNA regions is indicative of a neoplastic large intestine or breast cell or a cell predisposed to the onset of a neoplastic state.

In still another aspect there is provided a method of screening for the onset or predisposition to the onset of a large intestine or breast neoplasm in an individual, said method comprising assessing the methylation status of a DNA region selected from one or both of the regions defined by Hg19 coordinates Chr6:163834393-163834519 or Chr6: 163834393-163834455 in a biological sample from said individual wherein a higher level of methylation of one or both of these DNA regions is indicative of a neoplastic large intestine or breast cell or a cell predisposed to the onset of a neoplastic state.

In yet still another aspect there is provided a method of screening for the onset or predisposition to the onset of a large intestine, or breast neoplasm in an individual, said method comprising assessing the methylation of one or more cytosine residues selected from:

| Chr6: 163834330 | Chr6: 163834332 | Chr6: 163834357 |
| Chr6: 163834373 | Chr6: 163834384 | Chr6: 163834390 |
| Chr6: 163834392 | Chr6: 163834406 | Chr6: 163834412 |
| Chr6: 163834419 | Chr6: 163834443 | Chr6: 163834448 |
| Chr6: 163834452 | Chr6: 163834464 | Chr6: 163834483 |
| Chr6: 163834653 | Chr6: 163834660 | Chr6: 163834672 |
| Chr6: 163834675 | Chr6: 163834678 | Chr6: 163834681 |
| Chr6: 163834815 | Chr6: 163834824 | Chr6: 163834835 |
| Chr6: 163834840 | Chr6: 163834853 | Chr6: 163834855 |
| Chr6: 163834858 | Chr6: 163834863 | Chr6: 163834869 |
| Chr6: 163834872 | | | or a corresponding cytosine at position n+1 on the opposite DNA strand, in a biological sample from said individual wherein a higher level of methylation of one or more of said residues relative to the methylation level of a corresponding residue in a control sample is indicative of a neoplastic large intestine or breast cell or a cell predisposed to the onset of a neoplastic state.

In a further aspect, the increased methylation in a DNA region of the present invention is determined using a process comprising:

(i) treating the DNA derived from a biological sample with a compound that selectively mutates a non-methylated cytosine residue under conditions sufficient to induce mutagenesis;
(ii) amplifying the DNA of step (i) using primers designed to amplify a DNA region defined by one of SEQ ID NOs:1, 2, 3 or 4;
(iii) sequencing the amplification product of step (ii) to identify the presence in the DNA from said test sample of one or more cytosine residues which have not undergone mutation relative to the corresponding mutated residues in DNA from a control sample.

In another aspect, said mutagenesis is induced with bisulfite or equivalent agent and unmethylated cytosine residues are converted to uracil.

Another aspect of the present invention is directed to a method of screening for the onset or predisposition to the onset of a large intestine or breast neoplasm in an individual, said method comprising assessing the level of expression of the DNA region defined by Hg19 coordinates Chr6: 163834295-163834500 in a biological sample from said individual wherein a lower level of expression of said DNA region relative to control levels is indicative of a neoplastic large intestine or breast cell or a cell predisposed to the onset of a neoplastic state.

Another aspect of the present invention provides a diagnostic kit for assaying biological samples comprising one or more agents for detecting the marker of the present invention and reagents useful for facilitating the detection by said agents. Further means may also be included, for example, to receive a biological sample. The agent may be any suitable detecting molecule.

In one embodiment, said kit comprises one or more nucleic acid molecules corresponding to SEQ ID NOs:5, 6, 7, 8, 9, 10, 11 or 12, or substantially similar nucleic acid molecule. As detailed hereinbefore, these sequences are useful as the standards (controls) against which the product amplified from the test sample is assessed.

In another embodiment, said kit comprises one or more amplification primer sets which primer sets correspond to the sequences as follows:
(i) SEQ ID NOs:13 and 14 or substantially similar sequences;
(ii) SEQ ID Nos:13, 14 and 15 or substantially similar sequences;
(iii) SEQ ID NOs: 18 and 19 or substantially similar sequences;
(iv) SEQ ID NOs:20 and 21 or substantially similar sequences.

BRIEF DESCRIPTION OF THE DRAWINGS

FIG. 2: SEQ ID NO:2 with methylation positions indicated.

Solid lines: proportion of methylation measured in 10 colorectal cancer specimens.
Dashed lines: proportion of methylation measured in 10 normal colon specimens.
FIG. 3 depicts the SEQ ID NO: 1 and 2 sequences together with the chromosomal location-numbering of LOC100526820.

DETAILED DESCRIPTION OF THE INVENTION

Figure 1:
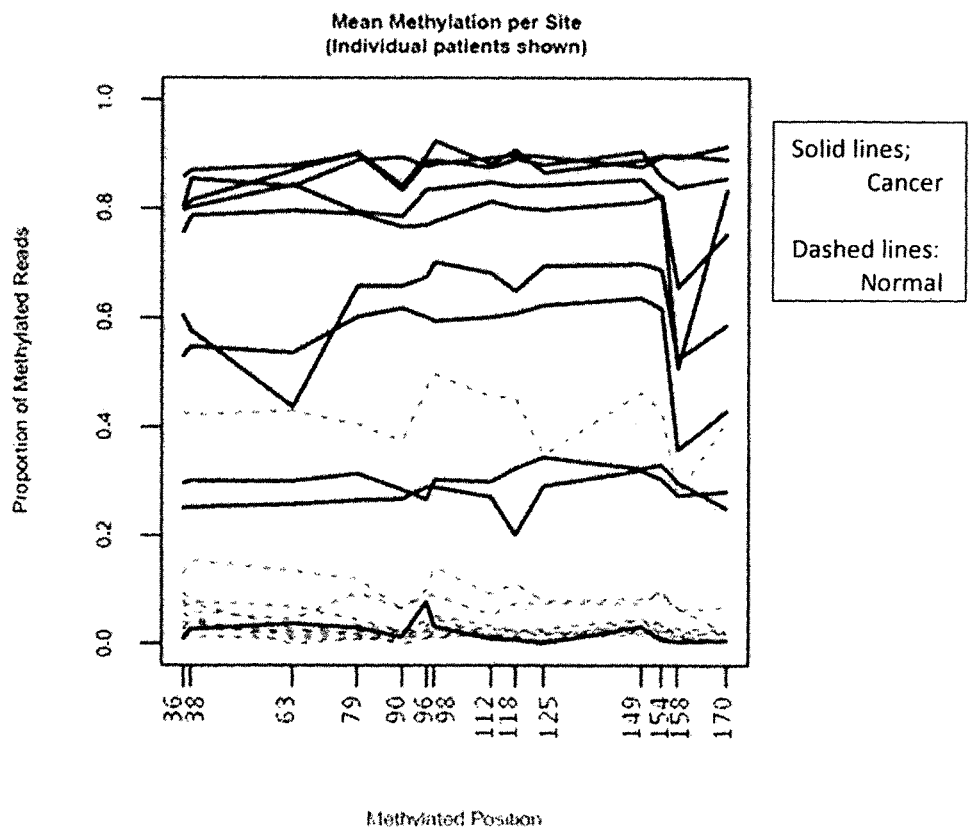
FIG. 1: SEQ ID NO:1 with methylation positions indicated.
Solid lines: proportion of methylation measured in 10 colorectal cancer specimens.
Dashed lines: proportion of methylation measured in 10 normal colon specimens.

The present invention is predicated, in part, on the elucidation of DNA methylation status which characterises large intestine and breast neoplasms. This finding has now facilitated the development of routine means of screening for the onset or predisposition to the onset of a large intestine or breast neoplasm based on increased methylation of the LOC100526820 DNA region relative to control levels. In accordance with the present invention, it has been determined that this DNA region is modulated, in terms of differential changes to its levels of methylation, depending on whether or not the cell in issue is neoplastic or not. It should be understood that the DNA region in issue is described herein both by reference to its name and its chromosomal coordinates. To the extent that the chromosomal coordinates corresponding to a DNA region is listed, this is consistent with the human genome database version Hg19 which was released in February 2009 (herein referred to as "Hg19 coordinates").

Accordingly, one aspect of the present invention is directed to a method of screening for the onset or predisposition to the onset of a large intestine or breast neoplasm in an individual, said method comprising assessing the methylation status of the DNA region defined by Hg19 coordinates Chr6: 163834097-163834982 in a biological sample from said individual wherein a higher level of methylation of said DNA region relative to control levels is indicative of a neoplastic large intestine or breast cell or a cell predisposed to the onset of a neoplastic state.

Reference to "large intestine" should be understood as a reference to a cell derived from one of the eight anatomical regions of the large intestine, which regions commence after the terminal region of the ileum, these being:
(i) the cecum;
(ii) the ascending colon;
(iii) the transverse colon;
(iv) the descending colon;
(v) the sigmoid colon;
(vi) the rectum;
(vii) the splenic flexure; and
(viii) the hepatic flexure.

Without limiting the present invention to any one theory or mode of action, the mammalian breast is a structurally dynamic organ which varies with age, menstrual cycle and reproductive status. It is a branched tubuloalveolar gland exhibiting secretory acinii which are grouped with inner lobules and drain into intralobular ducts which in turn drain into interlobular ducts. The lobules are organised into 15-20 lobes, each of which empty into separate lactiferous sinuses and from there into lactiferous ducts. The intralobular stroma consists of a loose connective tissue with a zone of hormone sensitive fibroblasts surrounding the lobular epithelial components. These are thought to take part in epithelial/basement membrane/stromal inductive interactions during morphogenesis and differentiation. The breast undergoes unique differentiative and proliferative development during the various life cycle stages of an individual. Accordingly, it should be understood that reference to the breast is a reference to the cells comprising the breast at any stage of its development including prepubescent, pubescent, prenatal, postnatal/lactating and post-menopausal stages. In this regard, it should also be understood that any given population of cells may be only transiently present in the breast, such as those which are generated during pregnancy for the purpose of facilitating lactation.

Reference to "neoplasm" should be understood as a reference to a lesion, tumour or other encapsulated or unencapsulated mass or other form of growth which comprises neoplastic cells. A "neoplastic cell" should be understood as a reference to a cell exhibiting abnormal growth. The term "growth" should be understood in its broadest sense and includes reference to proliferation. In this regard, an example of abnormal cell growth is the uncontrolled proliferation of a cell. Another example is failed apoptosis in a cell, thus prolonging its usual life span. The neoplastic cell may be a benign cell or a malignant cell. In a preferred embodiment, the subject neoplasm is an adenoma or an adenocarcinoma. Without limiting the present invention to any one theory or mode of action, an adenoma is generally a benign tumour of epithelial origin which is either derived from epithelial tissue or exhibits clearly defined epithelial structures. These structures may take on a glandular appearance. It can comprise a malignant cell population within the adenoma, such as occurs with the progression of a benign adenoma or benign neoplastic lesion to a malignant adenocarcinoma.

Preferably, said neoplastic cell is an adenoma or adenocarcinoma and even more preferably a colorectal or breast adenoma or adenocarcinoma.

Reference to "DNA region" should be understood as a reference to a specific section of genomic DNA. These DNA regions are specified by reference to a set of chromosomal coordinates, these being understood by the person of skill in the art. As detailed hereinbefore, the chromosomal coordinates for the DNA regions specified herein correspond to the Hg19 version of the genome. In general, a gene can be routinely identified by reference to its chromosomal location, via which its sequences can be routinely obtained. It should also be understood that reference to the DNA region Chr6:163834097-163834982 is interchangeably herein referred to by the name LOC100526820. The 886 nucleotide reverse strand sequence of this locus is provided in SEQ ID NO:17.

Other DNA regions, which fall within this locus are disclosed herein. These are as follows:

(i) Chr6:163834295-163834500, the nucleotide sequence of which is:

(SEQ ID NO: 1)
atctgtaaaa atgttgactt ctgcttttca gactacgcgc acagcctctt tatttcctac tgcggcttca ttccctcacg gaacactgac gccatcgcga aggaagcatt tcgagcacga ctgacgctcc ccttattatt tgctaagccg ctgcgctcgg gtctggctac gatttgcttt cagaataacg ggaaggtgca acaaga;

(ii) Chr6:163834621-163834906, the nucleotide sequence of which is:

(SEQ ID NO: 2)
gccgtgctgc tttccagcct ctcagcaaat cacgaacacc gaaagaagcc acggcggcga cgggaggggc gtcgcgcgtg -continued
cttccctcgg cgacaaagcg ggagccgggc gcgccggccg agggcgcccg gcgcagagtc ccgcagaggc ggacgccgcg gcacgcgcct cgaaaagcct caaactctta tcctcggctc tcccgcccca cctccgcccc gcagccaaga cccgcgccgt ggcgggcccg acggccaagg aaagcccacc agccctccgc accgtg;

(iii) Chr6:163834393-163834455, the nucleotide sequence of which is:

(SEQ ID NO: 3)
gaaggaagcatttcgagcacgactgacgctccccttattattt gctaagccgctgcgctcggg;

(iv) Chr6:163834393-163834519, the nucleotide sequence of which is:

(SEQ ID NO: 4)
gaaggaagcatttcgagcacgactgacgctccccttattatttg etaagccgctgcgctegggtctggctacgatttgetttcagaat aacgggaaggtgcaacaagatcgcttccctagaggcgcg.

SEQ ID NOs: 1 and 2 represent two discrete regions within the LOC 100526820 locus. SEQ ID NOs:3 and 4 represent two regions within SEQ ID NO:1, with the SEQ ID NO:3 region in fact falling within the longer SEQ ID NO:4 region. All of these regions are discussed in more detail hereafter.

Reference to each of the DNA regions detailed above should be understood as a reference to all forms of the molecules and to fragments or variants thereof. As would be appreciated by the person of skill in the art, some DNA regions are known to exhibit allelic variation between individuals or single nucleotide polymorphisms. SNPs encompass insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the DNA regions described herein. Accordingly, the present invention should be understood to extend to such variants which, in terms of the present diagnostic applications, achieve the same outcome despite the fact that minor genetic variations between the actual nucleic acid sequences may exist between individuals. The present invention should therefore be understood to extend to all forms of DNA which arise from any other mutation, polymorphic or allelic variation.

It should be understood that the "individual" who is the subject of testing may be any human or non-human mammal. Examples of non-human mammals includes primates, livestock animals (e.g. horses, cattle, sheep, pigs, donkeys), laboratory test animals (e.g. mice, rats, rabbits, guinea pigs), companion animals (e.g. dogs, cats) and captive wild animals (e.g. deer, foxes). Preferably the mammal is a human.

According to this embodiment there is provided a method of screening for the onset or predisposition to the onset of a large intestine or breast neoplasm in a human, said method comprising assessing the methylation status of the DNA region defined by Hg19 coordinates Chr6: 163834097-163834982 in a biological sample from said individual wherein a higher level of methylation of said DNA region relative to control levels is indicative of a neoplastic large intestine or breast cell or a cell predisposed to the onset of a neoplastic state.

Without limiting the present invention to any one theory or mode of action, although measuring the methylation levels across LOC100526820 is diagnostic of a large intestine neoplastic or breast condition, it has been determined that two discrete regions within LOC100526820 are particularly useful in this regard since these regions contain a high density of CpG dinucleotides which are frequently hypermethylated in large intestine and breast neoplasias, such as colorectal cancers.

Accordingly, one embodiment of the present invention is directed to a method of screening for the onset or predisposition to the onset of a large intestine or breast neoplasm in an individual, said method comprising assessing the methylation status of a DNA region selected from one or both of the regions defined by Hg19 coordinates Chr6: 163834295-163834500 or Chr6:163834621-163834906 in a biological sample from said individual wherein a higher level of methylation of one or both of these DNA regions is indicative of a neoplastic large intestine or breast cell or a cell predisposed to the onset of a neoplastic state.

In still another embodiment, the DNA region which is the subject of analysis is Chr6:163834393-163834519 (SEQ ID NO:4) which falls within the SEQ ID NO:1 region or Chr6:163834393-163834455 (SEQ ID NO:3) which falls within the SEQ ID NO:4 region. In one particular embodiment, PCR based assays have been developed and applied in the context of these two smaller DNA regions. These are discussed in more detail hereafter.

According to this embodiment there is provided a method of screening for the onset or predisposition to the onset of a large intestine or breast neoplasm in an individual, said method comprising assessing the methylation status of a DNA region selected from one or both of the regions defined by Hg19 coordinates Chr6:163834393-163834519 or Chr6: 163834393-163834455 in a biological sample from said individual wherein a higher level of methylation of one or both of these DNA regions is indicative of a neoplastic large intestine or breast cell or a cell predisposed to the onset of a neoplastic state.

In another embodiment, said neoplastic cell is an adenoma or adenocarcinoma and even more preferably a colorectal or breast adenoma or adenocarcinoma.

Without limiting the present invention to any one theory or mode of action, DNA methylation is universal in bacteria, plants, and animals. DNA methylation is a type of chemical modification of DNA that is stable over rounds of cell division but does not involve changes in the underlying DNA sequence of the organism. Chromatin and DNA modifications are two important features of epigenetics and play a role in the process of cellular differentiation, allowing cells to stably maintain different characteristics despite containing the same genomic material. In eukaryotic organisms DNA methylation occurs only at the number 5 carbon of the cytosine pyrimidine ring. In mammals, DNA methylation occurs mostly at the number 5 carbon of the cytosine of a CpG dinucleotide. CpG dinucleotides comprise approximately 1% human genome.

70%-80% of all CpGs are methylated. CpGs may be grouped in clusters called "CpG islands" that are present in the 5' regulatory regions of many genes and are frequently unmethylated. In many disease processes such as cancer, gene promoters and/or CpG islands acquire abnormal hypermethylation, which is associated with heritable transcriptional silencing. DNA methylation may impact the transcription of genes in two ways. First, the methylation of DNA may itself physically impede the binding of transcriptional proteins to the gene, thus blocking transcription. Second, methylated DNA may be bound by proteins known as Methyl-CpG-binding domain proteins (MBDs). MBD proteins then recruit additional proteins to the locus, such as histone deacetylases and other chromatin remodelling proteins that can modify histones, thereby forming compact, inactive chromatin termed silent chromatin. This link between DNA methylation and chromatin structure is very important. In particular, loss of Methyl-CpG-binding Protein 2 (MeCP2) has been implicated in Rett syndrome and Methyl-CpG binding domain protein 2 (MBD2) mediates the transcriptional silencing of hypermethylated genes in cancer.

In humans, the process of DNA methylation is carried out by three enzymes, DNA methyltransferase 1, 3a and 3b (DNMT1, DNMT3a, DNMT3b). It is thought that DNMT3a and DNMT3b are the de novo methyltransferases that set up DNA methylation patterns early in development. DNMT1 is the proposed maintenance methyltransferase that is responsible for copying DNA methylation patterns to the daughter strands during DNA replication. DNMT3L is a protein that is homologous to the other DNMT3s but has no catalytic activity. Instead, DNMT3L assists the de novo methyltransferases by increasing their ability to bind to DNA and stimulating their activity. Finally, DNMT2 has been identified as an "enigmatic" DNA methylstransferase homolog, containing all 10 sequence motifs common to all DNA methyltransferases; however, DNMT2 may not methylate DNA but instead has been shown to methylate a small RNA.

"Methylation status" should therefore be understood as a reference to the presence, absence and/or quantity of methylation at a particular nucleotide, or nucleotides, within a DNA region. The methylation status of a particular DNA sequence (e.g. DNA region as described herein) can indicate the methylation state of every base in the sequence or can indicate the methylation state of a subset of the base pairs (e.g., of cytosines) or the methylation state of one or more specific restriction enzyme recognition sequences within the sequence, or can indicate information regarding regional methylation density within the sequence without providing precise information of where in the sequence the methylation occurs. The methylation status can optionally be represented or indicated by a "methylation value." A methylation value can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of the methylation status. This is of particular use when it is desirable to compare the methylation status of a sequence in a sample to a threshold value.

The method of the present invention is predicated on the comparison of the level of methylation of specific DNA regions of a biological sample with the control methylation levels of these DNA regions. The "control level" is the "normal level", which is the level of methylation of the DNA region of a corresponding large intestine or breast cell or cellular population which is not neoplastic or in another biological sample, for example blood plasma, from which DNA may be isolated for assay.

The normal (or "non-neoplastic") methylation level may be determined using non-neoplastic tissues derived from the same individual who is the subject of testing. However, it would be appreciated that this may be quite invasive for the individual concerned and it is therefore likely to be more convenient to analyse the test results relative to a standard result which reflects individual or collective results obtained from individuals other than the patient in issue. This latter form of analysis is in fact the preferred method of analysis since it enables the design of kits which require the collection and analysis of a single biological sample, being a test sample of interest. The standard results which provide the normal methylation level may be calculated by any suitable means which would be well known to the person of skill in the art. For example, a population of normal tissues can be assessed in terms of the level of methylation of the genes of the present invention, thereby providing a standard value or range of values against which all future test samples are analysed. It should also be understood that the normal level may be determined from the subjects of a specific cohort and for use with respect to test samples derived from that cohort. Accordingly, there may be determined a number of standard values or ranges which correspond to cohorts which differ in respect of characteristics such as age, gender, ethnicity or health status. Said "normal level" may be a discrete level or a range of levels. An increase in the methylation level of the subject genes relative to normal levels is indicative of the tissue being neoplastic.

The term "methylation" shall be taken to mean the presence of a methyl group added by the action of a DNA methyl transferase enzyme to a cytosine base or bases in a region of nucleic acid, e.g. genomic DNA. As described herein, there are several methods known to those skilled in the art for determining the level or degree of methylation of nucleic acid.

By "higher level" is meant that there are a higher number of methylated CpG dinucleotides in the subject diagnosed than in a control sample, that is, either the proportion of DNA molecules methylated at a particular CpG site is higher or there are a higher number of separate CpG sites methylated in the subject. It should be understood that the terms "enhanced" and "increased" are used interchangeably with the term "higher". The present invention is not to be limited by a precise number of methylated residues that are considered to be diagnostic of neoplasia in a subject, because some variation between patient samples will occur. The present invention is also not limited by positioning of the methylated residue. Nevertheless, a number of specific cytosine residues have been identified which undergo hypermethylation in the context of large intestine neoplasms, in particular adenomas and benign neoplastic lesions. These are localised to the LOC100526820 regions defined by SEQ ID-NOs:1 and 2. In one embodiment, therefore, a screening method can be employed which is specifically directed to assessing the methylation status of one or more of either these residues or the corresponding cytosine at position n+1 on the opposite DNA strand.

According to this embodiment there is provided a method of screening for the onset or predisposition to the onset of a large intestine or breast neoplasm in an individual, said method comprising assessing the methylation of one or more cytosine residues selected from:

| | | |
|---|---|---|
| Chr6: 163834330 | Chr6: 163834332 | Chr6: 163834357 |
| Chr6: 163834373 | Chr6: 163834384 | Chr6: 163834390 |

-continued

| | | |
|---|---|---|
| Chr6: 163834392 | Chr6: 163834406 | Chr6: 163834412 |
| Chr6: 163834419 | Chr6: 163834443 | Chr6: 163834448 |
| Chr6: 163834452 | Chr6: 163834464 | Chr6: 163834483 |
| Chr6: 163834653 | Chr6: 163834660 | Chr6: 163834672 |
| Chr6: 163834675 | Chr6: 163834678 | Chr6: 163834681 |
| Chr6: 163834815 | Chr6: 163834824 | Chr6: 163834835 |
| Chr6: 163834840 | Chr6: 163834853 | Chr6: 163834855 |
| Chr6: 163834858 | Chr6: 163834863 | Chr6: 163834869 |
| Chr6: 163834872 | | | or a corresponding cytosine at position n+1 on the opposite DNA strand, in a biological sample from said individual wherein a higher level of methylation of one or more of said residues relative to the methylation level of a corresponding residue in a control sample is indicative of a neoplastic large intestine or breast cell or a cell predisposed to the onset of a neoplastic state.

These chromosome 6 positions are numbered by reference to the SEQ ID NO:1 and 2 sequences which are depicted in FIG. 3.

Without limiting the present invention to any one theory or mode of action, the development of neoplasia involves both genetic changes (point mutations, deletions, gene amplifications or arrangements) as well as a range of epigenetic changes, including DNA methylation and altered histone modifications at specific gene loci. The most extensively characterised of these changes is the hypermethylation of gene promoters of CpG islands. As detailed earlier, such hypermethylation is frequently associated with silencing of gene expression. In many cases this methylation-associated gene silencing is understood to play an important role in the development of the neoplasia, eg. through silencing of tumour suppressor genes such as p16 or Rb, or of DNA repair genes, eg. MLH1 or MGMT.

Genome-wide techniques for analysis of DNA methylation are increasingly being used to identify changes in DNA methylation in different cell types or disease conditions including cancer, with different biochemical and informatic approaches identifying overlapping sets of DNA methylation changes (Robinson et al. *Epigenomics* 2:587-98 (2010)). Bisulfite-tag technology was used in the context of the present invention to produce separate methylated and unmethylated fractions of DNA based on their methylation status at CpG sites within Msp1 (CCGG) or Taq1 (TCGA) restriction enzyme sites.

The detection method of the present invention can be performed on any suitable biological sample. To this end, reference to a "biological sample" should be understood as a reference to any sample of biological material derived from an animal such as, but not limited to, cellular material, biofluids (eg. blood), faeces, tissue biopsy specimens, surgical specimens or fluid which has been introduced into the body of an animal and subsequently removed (such as, for example, the solution retrieved from an enema wash). The biological sample which is tested according to the method of the present invention may be tested directly or may require some form of treatment prior to testing. For example, a biopsy or surgical sample may require homogenisation prior to testing or it may require sectioning for in situ testing of the qualitative expression levels of individual genes. Alternatively, a cell sample may require permeabilisation prior to testing. Further, to the extent that the biological sample is not in liquid form, (if such form is required for testing) it may require the addition of a reagent, such as a buffer, to mobilise the sample.

To the extent that the DNA region of interest is present in a biological sample, the biological sample may be directly tested or else all or some of the nucleic acid present in the biological sample may be isolated prior to testing. In yet another example, the sample may be partially purified or otherwise enriched prior to analysis. For example, to the extent that a biological sample comprises a very diverse cell population, it may be desirable to enrich for a sub-population of particular interest. It is within the scope of the present invention for the target cell population or molecules derived therefrom to be treated prior to testing, for example, inactivation of live virus. It should also be understood that the biological sample may be freshly harvested or it may have been stored (for example by freezing) prior to testing or otherwise treated prior to testing (such as by undergoing culturing).

The choice of what type of sample is most suitable for testing in accordance with the method disclosed herein will be dependent on the nature of the situation. Preferably, said sample is a faecal (stool) sample, enema wash, surgical resection, tissue biopsy or blood sample (e.g. whole blood, serum or plasma).

More preferably, said biological sample is a blood sample, biopsy sample or stool sample.

As detailed hereinbefore, the present invention is designed to screen for a neoplastic cell or cellular population, which is located in the large intestine or the breast. Accordingly, reference to "cell or cellular population" should be understood as a reference to an individual cell or a group of cells. Said group of cells may be a diffuse population of cells, a cell suspension, an encapsulated population of cells or a population of cells which take the form of tissue.

Reference to the "onset" of a neoplasm, such as adenoma or adenocarcinoma, should be understood as a reference to one or more cells of that individual exhibiting dysplasia. In this regard, the adenoma or adenocarcinoma may be well developed in that a mass of dysplastic cells has developed. Alternatively, the adenoma or adenocarcinoma may be at a very early stage in that only relatively few abnormal cell divisions have occurred at the time of diagnosis. The present invention also extends to the assessment of an individual's predisposition to the development of a neoplasm, such as an adenoma or adenocarcinoma. Without limiting the present invention in any way, changed methylation levels may be indicative of that individual's predisposition to developing a neoplasia, such as the future development of an adenoma or adenocarcinoma or another adenoma or adenocarcinoma.

Although the preferred method is to assess methylation levels for the purpose of diagnosing neoplasia development or predisposition thereto, the detection of converse changes in the levels of said methylation may be desired under certain circumstances, for example, to monitor the effectiveness of therapeutic or prophylactic treatment directed to modulating a neoplastic condition, such as adenoma or adenocarcinoma development. For example, where elevated levels of methylation indicate that an individual has developed a condition characterised by adenoma or adenocarcinoma development, screening for a decrease in the levels of methylation subsequently to the onset of a therapeutic treatment regime may be utilised to indicate successful clearance of the neoplastic cells. In another example, one can use this method to test the tissue at the margins of a tumour resection in order to determine whether the full margin of the tumour has been removed.

The present method can therefore be used in the diagnosis, prognosis, classification, prediction of disease risk, detection of recurrence of disease, and selection of treatment of a number of types of neoplasias. A cancer at any stage of progression can be detected, such as primary, metastatic, and recurrent cancers.

The present invention provides methods for determining whether or not a mammal (e.g., a human) has a neoplasia of the large intestine or breast, whether or not a biological sample taken from a mammal contains neoplastic cells or DNA derived from neoplastic cells, estimating the risk or likelihood of a mammal developing a neoplasm, monitoring the efficacy of anti-cancer treatment, or selecting the appropriate anti-cancer treatment in a mammal with cancer. Such methods are based on the determination that neoplastic cells have a different methylation status than normal cells in the DNA regions described herein. Accordingly, by determining whether or not a cell contains differentially methylated sequences in the DNA regions as described herein, it is possible to determine whether or not the cell is neoplastic.

The method of the invention can be used to evaluate individuals known or suspected to have a neoplasia or as a routine clinical test, i.e., in an individual not necessarily suspected to have a neoplasia. Further diagnostic assays can be performed to confirm the status of neoplasia in the individual and to confirm the type of neoplasia. For example, if a blood test result indicates the presence of a neoplasia, it may be necessary to conduct further screening to establish whether that neoplasia is breast or large intestine in origin.

Further, the present methods may be used to assess the efficacy of a course of treatment. For example, the efficacy of an anti-cancer treatment can be assessed by monitoring DNA methylation of the sequences described herein over time in a mammal having cancer. For example, a reduction or absence of methylation in any of the diagnostic sequences of the invention in a biological sample taken from a mammal following a treatment, compared to a level in a sample taken from the mammal before, or earlier in, the treatment, indicates efficacious treatment.

The method of the present invention is therefore useful as a one-time test or as an on-going monitor of those individuals thought to be at risk of neoplasia development or as a monitor of the effectiveness of therapeutic or prophylactic treatment regimes directed to inhibiting or otherwise slowing neoplasia development. In these situations, mapping the modulation of methylation levels in any one or more classes of biological samples is a valuable indicator of the status of an individual or the effectiveness of a therapeutic or prophylactic regime which is currently in use. Accordingly, the method of the present invention should be understood to extend to monitoring for increases or decreases in methylation levels in an individual relative to their normal level (as hereinbefore defined), or relative to one or more earlier methylation levels determined from a biological sample of said individual.

The methods for detecting neoplasia can comprise the detection of one or more other cancer-associated polynucleotide or polypeptides sequences. Accordingly, detection of methylation by the method of the invention can be used either alone or in combination with other screening methods for the diagnosis or prognosis of neoplasia.

Any method for detecting DNA methylation can be used in the methods of the present invention. A number of methods are available for detection of differentially methylated DNA at specific loci in either primary tissue samples or in patient samples such as blood, urine, stool or saliva (reviewed in Kristensen and Hansen, *Clin Chem.* 55:1471-83, 2009; Ammerpohl et al. *Biochim Biophys Acta.* 1790:

847-62, 2009; Shames et al. *Cancer Lett.* 251:187-98, 2007; Clark et al. *Nat Protoc.* 1:2353-64, 2006). For analysis of the proportion or extent of DNA methylation in a target gene, DNA is normally treated with sodium bisulfite and regions of interest amplified using primers and PCR conditions that will amplify independently of the methylation status of the DNA. The methylation of the overall amplicon or individual CpG sites can then be assessed by sequencing, including pyrosequencing, restriction enzyme digestion (COBRA) or by melting curve analysis. Alternatively ligation-based methods for analysis of methylation at specific CpG sites may be used. Detection of aberrantly methylated DNA released from tumours and into bodily fluids is being developed as a means of cancer diagnosis. Here, in the case of hypermethylated sequences, it is necessary to use sensitive methods that allow the selective amplification of the methylated DNA sequence from a background of normal cellular DNA that is unmethylated. Such methods based on bisulfite-treated DNA include, for example methylation selective PCR (MSP), Heavymethyl PCR, Headloop PCR and Helper-dependent chain reaction (PCT/AU2008/001475).

Briefly, in some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. patent application Ser. Nos. 10/971,986; 11/071,013; and 10/971,339. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In some embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. A methylation-sensitive enzyme is one which cuts DNA if its recognition sequence is unmethylated while a methylation-dependent enzyme cuts DNA if its recognition sequence is methylated. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. patent application Ser. No. 10/971,986.

Kits for the above methods can include, e.g., one or more of methylation-dependent restriction enzymes, methylation-sensitive restriction enzymes, amplification (e.g., PCR) reagents, probes and/or primers.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol. Biotechnol.* 20(2): 163-79 (2002). Amplifications may be monitored in "real time."

Additional methods for detecting DNA methylation can involve genomic sequencing before and after treatment of the DNA with bisulfite. See, e.g., Frommer et al., *Proc. Natl. Acad. Sci. USA* 89:1827-1831 (1992). When sodium bisulfite is contacted to DNA, unmethylated cytosine is converted to uracil, while methylated cytosine is not modified.

In some embodiments, restriction enzyme digestion of PCR products amplified from bisulfite-converted DNA is used to detect DNA methylation. See, e.g., Sadri & Hornsby, *Nucl. Acids Res.* 24:5058-5059 (1996); Xiong & Laird, *Nucleic Acids Res.* 25:2532-2534 (1997).

In some embodiments, a methylation-specific PCR ("MSP") reaction is used alone or in combination with other methods to detect DNA methylation. An MSP assay entails initial modification of DNA by sodium bisulfite, converting all unmethylated, but not methylated, cytosines to uracil, and subsequent amplification with primers specific for methylated versus unmethylated DNA. See, Herman et al., *Proc. Natl. Acad. Sci. USA* 93:9821-9826, (1996); U.S. Pat. No. 5,786,146.

In some embodiments, a MethyLight assay is used alone or in combination with other methods to detect DNA methylation (see, Eads et al., *Cancer Res.* 59:2302-2306 (1999)). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of methylated DNA, (or alternatively to unmethylated sequences) amplification can indicate methylation status of sequences where the primers hybridize. Furthermore, the amplification product can be detected with a probe that specifically binds to a sequence resulting from bisulfite treatment of a methylated (or unmethylated) DNA. If desired, both primers and probes can be used to detect methylation status. Thus, kits for use with MethyLight can include sodium bisulfite as well as primers or detectably-labelled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In some embodiments, a Ms-SNuPE (Methylation-sensitive Single Nucleotide Primer Extension) reaction is used alone or in combination with other methods to detect DNA methylation (see, Gonzalgo & Jones, *Nucleic Acids Res.* 25:2529-2531 (1997)). The Ms-SNuPE technique is a quantitative method for assessing methylation differences at specific CpG sites based on bisulfite treatment of DNA, followed by single-nucleotide primer extension (Gonzalgo & Jones, supra). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest.

Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labelled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

Additional methylation detection methods include, but are not limited to, methylated CpG island amplification (see, Toyota et al., *Cancer Res.* 59:2307-12 (1999)), those described in, e.g., U.S. Patent Publication 2005/0069879; Rein, et al. *Nucleic Acids Res.* 26 (10): 2255-64 (1998); Olek, et al. *Nat. Genet.* 17(3): 275-6 (1997); and PCT Publication No. WO 00/70090, Headloop PCT and the Helper-dependent chain reaction.

More detailed information in relation to several of these generally described methods is provided below:

(a) Probe or Primer Design and/or Production

Several methods described herein for the diagnosis of a neoplasia use one or more probes and/or primers. Methods for designing probes and/or primers for use in, for example, PCR or hybridization are known in the art and described, for example, in Dieffenbach and Dveksler (Eds) (In: PCR Primer: A Laboratory Manual, Cold Spring Harbor Laboratories, NY, 1995). Furthermore, several software packages are publicly available that design optimal probes and/or primers for a variety of assays, e.g. Primer 3 available from the Center for Genome Research, Cambridge, Mass., USA.

Clearly, the potential use of the probe or primer should be considered during its design. For example, should the probe or primer be produced for use in a methylation specific PCR or ligase chain reaction (LCR) assay the nucleotide at the 3' end (or 5' end in the case of LCR) should preferably correspond to a methylated nucleotide in a nucleic acid.

Probes and/or primers useful for detection of a sequence associated with a neoplasia are assessed, for example, to determine those that do not form hairpins, self-prime or form primer dimers (e.g. with another probe or primer used in a detection assay). Furthermore, a probe or primer (or the sequence thereof) is often assessed to determine the temperature at which it denatures from a target nucleic acid (i.e. the melting temperature of the probe or primer, or Tm). Methods for estimating Tm are known in the art and described, for example, in Santa Lucia, *Proc. Natl. Acad. Sci. USA*, 95: 1460-1465, 1995 or Breslauer et al., *Proc. Natl. Acad. Sci. USA,* 83: 3746-3750, 1986.

Methods for producing/synthesizing a probe or primer of the present invention are known in the art. For example, oligonucleotide synthesis is described, in Gait (Ed) (In: Oligonucleotide Synthesis: A Practical Approach, IRL Press, Oxford, 1984). For example, a probe or primer may be obtained by biological synthesis (e.g. by digestion of a nucleic acid with a restriction endonuclease) or by chemical synthesis. For short sequences (up to about 100 nucleotides) chemical synthesis is preferable.

For longer sequences standard replication methods employed in molecular biology are useful, such as, for example, the use of M13 for single stranded DNA as described by Messing, *Methods Enzymol,* 101, 20-78, 1983. Other methods for oligonucleotide synthesis include, for example, phosphotriester and phosphodiester methods (Narang, et al. *Meth. Enzymol* 68: 90, 1979) and synthesis on a support (Beaucage, et al. *Tetrahedron Letters* 22: 1859-1862, 1981) as well as phosphoramidate technique, Caruthers, M. H., et al., "Methods in Enzymology," Vol. 154, pp. 287-314 (1988), and others described in "Synthesis and Applications of DNA and RNA," S. A. Narang, editor, Academic Press, New York, 1987, and the references cited therein. Probes comprising locked nucleic acid (LNA) are synthesized as described, for example, in Nielsen et al., *J. Chem. Soc. Perkin Trans.,* 1:3423, 1997; Singh and Wengel, *Chem. Commun.* 1247, 1998. While, probes comprising peptide-nucleic acid (PNA) are synthesized as described, for example, in Egholm et al., *Am. Chem. Soc.,* 114: 1895, 1992; Egholm et al., *Nature,* 365: 566, 1993; and Orum et al., *Nucl. Acids Res.,* 21: 5332, 1993.

(b) Methylation-Sensitive Endonuclease Digestion of DNA

In one example, the increased methylation in a sample is determined using a process comprising treating the nucleic acid with an amount of a methylation-sensitive restriction endonuclease enzyme under conditions sufficient for nucleic acid to be digested and then detecting the fragments produced. Exemplary methylation-sensitive endonucleases include, for example, HhaI or HpaII. Preferably, assays include internal controls that are digested with a methylation-insensitive enzyme having the same specificity as the methylation-sensitive enzyme employed. For example, the methylation-insensitive enzyme MspI is an isoschizomer of the methylation-sensitive enzyme HpaII.

Hybridization Assay Formats

In one example, the digestion of nucleic acid is detected by selective hybridization of a probe or primer to the undigested nucleic acid. Alternatively, the probe selectively hybridizes to both digested and undigested nucleic acid but facilitates differentiation between both forms, e.g., by electrophoresis. Suitable detection methods for achieving selective hybridization to a hybridization probe include, for example, Southern or other nucleic acid hybridization (Kawai et al., *Mol. Cell. Biol.* 14, 7421-7427, 1994; Gonzalgo et al., Cancer Res. 57, 594-599, 1997).

Suitable hybridization conditions are determined based on the melting temperature (Tm) of a nucleic acid duplex comprising the probe. The skilled artisan will be aware that optimum hybridization reaction conditions should be determined empirically for each probe, although some generalities can be applied. Preferably, hybridizations employing short oligonucleotide probes are performed at low to medium stringency. In the case of a GC rich probe or primer or a longer probe or primer a high stringency hybridization and/or wash is preferred. A high stringency is defined herein as being a hybridization and/or wash carried out in about 0.1.times.SSC buffer and/or about 0.1% (w/v) SDS, or lower salt concentration, and/or at a temperature of at least 65.degree. C., or equivalent conditions. Reference herein to a particular level of stringency encompasses equivalent conditions using wash/hybridization solutions other than SSC known to those skilled in the art.

In accordance with the present example, a difference in the fragments produced for the test sample and a negative control sample is indicative of the subject having a neoplasia. Similarly, in cases where the control sample comprises data from a tumor, cancer tissue or a cancerous cell or pre-cancerous cell, similarity, albeit not necessarily absolute identity, between the test sample and the control sample is indicative of a positive diagnosis (i.e. cancer).

Amplification Assay Formats

In an alternative example, the fragments produced by the restriction enzyme are detected using an amplification system, such as, for example, polymerase chain reaction (PCR), rolling circle amplification (RCA), inverse polymerase chain reaction (iPCR), in situ PCR (Singer-Sam et al., *Nucl. Acids Res.* 18:687, 1990), strand displacement amplification (SDA) or cycling probe technology.

Methods of PCR are known in the art and described, for example, by McPherson et al., PCR: A Practical Approach. (series eds, D. Rickwood and B. D. Hames), IRL Press Limited. Oxford. pp 1-253, 1991 and by Dieffenbach (ed) and Dveksler (ed) (In: PCR Primer: A Laboratory Manual, Cold Spring Harbour Laboratories, NY, 1995), the contents of which are each incorporated in their entirety by way of reference. Generally, for PCR two non-complementary nucleic acid primer molecules comprising at least about 18 nucleotides in length, and more preferably at least 20-30 nucleotides in length are hybridized to different strands of a nucleic acid template molecule at their respective annealing sites, and specific nucleic acid molecule copies of the template that intervene the annealing sites are amplified enzymatically. Amplification products may be detected, for example, using electrophoresis and detection with a detectable marker that binds nucleic acids. Alternatively, one or more of the oligonucleotides are labelled with a detectable marker (e.g. a fluorophore) and the amplification product detected using, for example, a lightcycler (Perkin Elmer, Wellesley, Mass., USA; Roche Applied Science, Indianapolis, Ind., USA).

Strand displacement amplification (SDA) utilizes oligonucleotide primers, a DNA polymerase and a restriction endonuclease to amplify a target sequence. The oligonucleotides are hybridized to a target nucleic acid and the polymerase is used to produce a copy of the region intervening the primer annealing sites. The duplexes of copied nucleic acid and target nucleic acid are then nicked with an endonuclease that specifically recognizes a sequence at the beginning of the copied nucleic acid. The DNA polymerase recognizes the nicked DNA and produces another copy of the target region at the same time displacing the previously generated nucleic acid. The advantage of SDA is that it occurs in an isothermal format, thereby facilitating high-throughput automated analysis.

Cycling Probe Technology uses a chimeric synthetic primer that comprises DNA-RNA-DNA that is capable of hybridizing to a target sequence. Upon hybridization to a target sequence the RNA-DNA duplex formed is a target for RNaseH thereby cleaving the primer. The cleaved primer is then detected, for example, using mass spectrometry or electrophoresis.

For primers that flank or are adjacent to a methylation-sensitive endonuclease recognition site, it is preferred that such primers flank only those sites that are hypermethylated in neoplasia to ensure that a diagnostic amplification product is produced. In this regard, an amplification product will only be produced when the restriction site is not cleaved, i.e., when it is methylated. Accordingly, detection of an amplification product indicates that the CpG dinucleotide/s of interest is/are methylated.

As will be known to the skilled artisan, the precise length of the amplified product will vary depending upon the distance between the primers. Clearly this form of analysis may be used to determine the methylation status of a plurality of CpG dinucleotides provided that each dinucleotide is within a methylation sensitive restriction endonuclease site. In these methods, one or more of the primers may be labelled with a detectable marker to facilitate rapid detection of amplified nucleic acid, for example, a fluorescent label (e.g. Cy5 or Cy3) or a radioisotope (e.g. $^{32}P$).

The amplified nucleic acids are generally analyzed using, for example, non-denaturing agarose gel electrophoresis, non-denaturing polyacrylamide gel electrophoresis, mass spectrometry, liquid chromatography (e.g. HPLC or dHPLC), or capillary electrophoresis. (e.g. MALDI-TOF). High throughput detection methods, such as, for example, matrix-assisted laser desorption/ionization time of flight (MALDI-TOF), electrospray ionization (ESI), mass spectrometry (including tandem mass spectrometry, e.g. LC MS/MS), biosensor technology, evanescent fiber-optics technology or DNA chip technology (e.g., WO98/49557; WO 96/17958; Fodor et al., *Science* 767-773, 1991; U.S. Pat. Nos. 5,143,854; and 5,837,832, the contents of which are all incorporated herein by reference), are especially preferred for all assay formats described herein. Alternatively, amplification of a nucleic acid may be continuously monitored using a melting curve analysis method as described herein and/or in, for example, U.S. Pat. No. 6,174,670, which is incorporated herein by reference.

(c) Other Assay Formats

In an alternative example, the increased methylation in a sample is determined by performing a process comprising treating chromatin containing the nucleic acid with an amount of DNaseI under conditions sufficient for nucleic acid to be digested and then detecting the fragments produced. This assay format is predicated on the understanding that chromatin containing methylated DNA, e.g., hyper methylated DNA, has a more tightly-closed conformation than non-hyper methylated DNA and, as a consequence, is less susceptible to endonuclease digestion by DNase I.

In accordance with this method, DNA fragments of different lengths are produced by DNase I digestion of methylated compared to non-methylated DNA. Such different DNA fragments are detected, for example, using an assay described earlier. Alternatively, the DNA fragments are detected using PCR-SSCP essentially as described, for example, in Gregory and Feil *Nucleic Acids Res.*, 27, e32i-e32iv, 1999. In adapting PCR-SSCP to the present invention, amplification primers flanking or comprising one or more CpG dinucleotides in a nucleic acid that are resistant to DNase I digestion in a neoplasia sample but not resistant to DNase I digestion in a healthy/normal control or healthy/normal test sample are used to amplify the DNase I-generated fragments. In this case, the production of a specific nucleic acid fragment using DNase I is diagnostic of neoplasia, because the DNA is not efficiently degraded. In contrast, template DNA from a healthy/normal subject sample is degraded by the action of DNase I and, as a consequence, amplification fails to produce a discrete amplification product. Alternative methods to PCR-SSCP, such as for example, PCR-dHPLC are also known in the art and contemplated by the present invention.

(d) Selective Mutagenesis of Non-Methylated DNA

In an alternative method the increased methylation in a sample is determined using a process comprising treating the nucleic acid with an amount of a compound that selectively mutates a non-methylated cytosine residue within a CpG dinucleotide under conditions sufficient to induce mutagenesis.

Preferred compounds mutate cytosine to uracil or thymidine, such as, for example, a salt of bisulfite, e.g., sodium bisulfite or potassium bisulfite (Frommer et al., *Proc. Natl. Acad. Sci. USA* 89, 1827-1831, 1992). Bisulfite treatment of DNA is known to distinguish methylated from non-methylated cytosine residues, by mutating cytosine residues that are not protected by methylation, including cytosine residues that are not within a CpG dinucleotide or that are positioned within a CpG dinucleotide that is not subject to methylation.

Sequence Based Detection

In one example, the presence of one or more mutated nucleotides or the number of mutated sequences is determined by sequencing mutated DNA. One form of analysis comprises amplifying mutated nucleic acid using an amplification reaction described herein, for example, PCR. The amplified, product is then directly sequenced or cloned and the cloned product sequenced. Methods for sequencing DNA are known in the art and include for example, the dideoxy chain termination method or the Maxam-Gilbert method (see Sambrook et al., Molecular Cloning, A Laboratory Manual (2nd Ed., CSHP, New York 1989) or Zyskind et al., Recombinant DNA Laboratory Manual, (Acad. Press, 1988)).

As the treatment of nucleic acid with a compound, such as, for example, bisulfite results in non-methylated cytosines being mutated to uracil (and hence thymidine after an amplification process), analysis of the sequence determines the presence or absence of a methylated nucleotide. For example, by comparing the sequence obtained using a control sample or a sample that has not been treated with bisulfite, or the known nucleotide sequence of the region of interest with a treated sample facilitates the detection of differences in the nucleotide sequence. Any thymine residue detected at the site of a cytosine in the treated sample compared to a control or untreated sample may be considered to be caused by mutation as a result of bisulfite treatment. Suitable methods for the detection of methylation using sequencing of bisulfite treated nucleic acid are described, for example, in Frommer et al., *Proc. Natl. Acad. Sci. USA* 89: 1827-1831, 1992 or Clark et al., *Nucl. Acids Res.* 22: 2990-2997, 1994.

In another method, the presence of a mutated or non-mutated nucleotide in a bisulfite treated sample is detected using pyrosequencing, such as, for example, as described in Uhlmann et al., Electrophoresis, 23: 4072-4079, 2002. Essentially this method is a form of real-time sequencing that uses a primer that hybridizes to a site adjacent or close to the site of a cytosine that is methylated. Following hybridization of the primer and template in the presence of a DNA polymerase each of four modified deoxynucleotide triphosphates are added separately according to a predetermined dispensation order. Only an added nucleotide that is complementary to the bisulfite treated sample is incorporated and inorganic pyrophosphate (PPi) is liberated. The PPi then drives a reaction resulting in production of detectable levels of light. Such a method allows determination of the identity of a specific nucleotide adjacent to the site of hybridization of the primer.

Methods of solid phase pyrosequencing are known in the art and reviewed in, for example. Landegren et al., *Genome Res.*, 8(8): 769-776, 1998. Such methods enable the high-throughput detection of methylation of a number of CpG dinucleotides.

A related method for determining the sequence of a bisulfite treated nucleotide is methylation-sensitive single nucleotide primer extension (Me-SnuPE) or SNaPmeth. Suitable methods are described, for example, in Gonzalgo and Jones *Nucl. Acids Res.*, 25:2529-2531 or Uhlmann et al., *Electrophoresis*, 23: 4072-4079, 2002. An oligonucleotide is used that hybridizes to the region of a nucleic acid adjacent to the site of a cytosine that is methylated. This oligonucleotide is then used in a primer extension protocol with a polymerase and a free nucleotide diphosphate or dideoxy-nucleotide triphosphate that corresponds to either or any of the possible bases that occur at this site following bisulfite treatment (i.e., thymine or cytosine). Preferably, the nucleotide-diphosphate is labelled with a detectable marker (e.g. a fluorophore). Following primer extension, unbound labelled nucleotide diphosphates are removed, e.g. using size exclusion chromatography or electrophoresis, or hydrolyzed, using for example, alkaline phosphatase, and the incorporation of the labelled nucleotide to the oligonucleotide is detected, indicating the base that is present at the site.

Clearly other high throughput sequencing methods are encompassed by the present invention. Such methods include, for example, solid phase minisequencing (as described, for example, in Southern et al., *Genomics*, 13: 1008-1017, 1992), or minisequencing with FRET (as described, for example, in Chen and Kwok, *Nucleic Acids Res.* 25: 347-353, 1997).

Restriction Endonuclease-Based Assay Format

In one method, the presence of a non-mutated sequence is detected using combined bisulfite restriction analysis (COBRA) essentially as described in Xiong and Laird, *Nucl. Acids Res.*, 25: 2532-2534, 2001. This method exploits the differences in restriction enzyme recognition sites between methylated and unmethylated nucleic acid after treatment with a compound that selectively mutates a non-methylated cytosine residue, e.g., bisulfite.

Following bisulfite treatment a region of interest comprising one or more CpG dinucleotides that are methylated and are included in a restriction endonuclease recognition sequence is amplified using an amplification reaction described herein, e.g., PCR. The amplified product is then contacted with the restriction enzyme that cleaves at the site of the CpG dinucleotide for a time and under conditions sufficient for cleavage to occur. A restriction site may be selected to indicate the presence or absence of methylation. For example, the restriction endonuclease TaqI cleaves the sequence TCGA, following bisulfite treatment of a non-methylated nucleic acid the sequence will be TTGA and, as a consequence, will not be cleaved. The digested and/or non-digested nucleic acid is then detected using a detection means known in the art, such as, for example, electrophoresis and/or mass spectrometry. The cleavage or non-cleavage of the nucleic acid is indicative of cancer in a subject. Clearly, this method may be employed in either a positive read-out or negative read-out system for the diagnosis of a cancer.

Positive Read-Out Assay Format

In one embodiment, the assay format of the invention comprises a positive read-out system in which DNA from a sample that has been treated, for example, with bisulfite is detected as a positive signal. Preferably, the non-hypermethylated DNA from a healthy or normal control subject is not detected or only weakly detected.

In a preferred embodiment, the increased methylation in a subject sample is determined using a process comprising:

(i) treating the nucleic acid with an amount of a compound that selectively mutates a non-methylated cytosine residue under conditions sufficient to induce mutagenesis thereby producing a mutated nucleic acid;

(ii) hybridizing a nucleic acid to a probe or primer comprising a nucleotide sequence that is complementary to a sequence comprising a methylated cytosine residue under conditions such that selective hybridization to the non-mutated nucleic acid occurs; and (iii) detecting the selective hybridization.

In this context, the term "selective hybridization" means that hybridization of a probe or primer to the non-mutated nucleic acid occurs at a higher frequency or rate, or has a higher maximum reaction velocity, than hybridization of the same probe or primer to the corresponding mutated sequence. Preferably, the probe or primer does not hybridize to the non-methylated sequence carrying the mutation(s) under the reaction conditions used.

Hybridization-Based Assay Format

In one embodiment, the hybridization is detected using Southern, dot blot, slot blot or other nucleic acid hybridization means (Kawai et al., *Mol. Cell. Biol.* 14:7421-7427, 1994; Gonzalgo et al., *Cancer Res.* 57, 594-599, 1997). Subject to appropriate probe selection, such assay formats are generally described herein above and apply mutatis mutandis to the presently described selective mutagenesis approach.

Preferably, a ligase chain reaction format is employed to distinguish between a mutated and non-mutated nucleic acid. Ligase chain reaction (described in EP 320,308 and U.S. Pat. No. 4,883,750) uses at least two oligonucleotide probes that anneal to a target nucleic acid in such a way that they are juxtaposed on the target nucleic acid. In a ligase chain reaction assay, the target nucleic acid is hybridized to a first probe that is complementary to a diagnostic portion of the target sequence (the diagnostic probe) e.g., a nucleic acid comprising one or more methylated CpG dinucleotide(s), and with a second probe that is complementary to a nucleotide sequence contiguous with the diagnostic portion (the contiguous probe), under conditions wherein the diagnostic probe remains bound substantially only to the target nucleic acid. The diagnostic and contiguous probes can be of different lengths and/or have different melting temperatures such that the stringency of the hybridization can be adjusted to permit their selective hybridization to the target, wherein the probe having the higher melting temperature is hybridized at higher stringency and, following washing to remove unbound and/or non-selectively bound probe, the other probe having the lower melting temperature is hybridized at lower stringency. The diagnostic probe and contiguous probe are then covalently ligated such as, for example, using T4 DNA ligase, to thereby produce a larger target probe that is complementary to the target sequence, and the probes that are not ligated are removed by modifying the hybridization stringency. In this respect, probes that have not been ligated will selectively hybridize under lower stringency hybridization conditions than probes that have been ligated. Accordingly, the stringency of the hybridization can be increased to a stringency that is at least as high as the stringency used to hybridize the longer probe, and preferably at a higher stringency due to the increased length contributed by the shorter probe following ligation.

In another example, one or both of the probes is labelled such that the presence or absence of the target sequence can be tested by melting the target-probe duplex, eluting the dissociated probe, and testing for the label(s). Where both probes are labelled, different ligands are used to permit distinction between the ligated and unligated probes, in which case the presence of both labels in the same eluate fraction confirms the ligation event. If the target nucleic acid is bound to a solid matrix e.g., in a Southern hybridization, slot blot, dot blot, or microchip assay format, the presence of both the diagnostic and contiguous probes can be determined directly.

Methylation specific microarrays (MSO) are also useful for differentiating between a mutated and non-mutated sequence. A suitable method is described, for example, in Adorjan et al, *Nucl. Acids Res.*, 30: e21, 2002. MSO uses nucleic acid that has been treated with a compound that selectively mutates a non-methylated cytosine residue (e.g., bisulfite) as template for an amplification reaction that amplifies both mutant and non-mutated nucleic acid. The amplification is performed with at least one primer that comprises a detectable label, such as, for example, a fluorophore, e.g., Cy3 or Cy5.

To produce a microarray for detection of mutated nucleic acid oligonucleotides are spotted onto, for example, a glass slide, preferably, with a degree of redundancy (for example, as described in Golub et al., *Science*, 286:531-537, 1999). Preferably, for each CpG dinucleotide analyzed two different oligonucleotides are used. Each oligonucleotide comprises a sequence $N_{2-16}CGN_{2-16}$ or $N_{2-16}TGN_{2-16}$ (wherein N is a number of nucleotides adjacent or juxtaposed to the CpG dinucleotide of interest) reflecting the methylated or non-methylated status of the CpG dinucleotides.

The labelled amplification products are then hybridized to the oligonucleotides on the microarray under conditions that enable detection of single nucleotide differences. Following washing to remove unbound amplification product, hybridization is detected using, for example, a microarray scanner. Not only does this method allow for determination of the methylation status of a large number of CpG dinucleotides, it is also semi-quantitative, enabling determination of the degree of methylation at each CpG dinucleotide analyzed. As there may be some degree of heterogeneity of methylation in a single sample, such quantification may assist in the diagnosis of cancer.

Amplification-Based Assay Format

In an alternative example, the hybridization is detected using an amplification system. In methylation-specific PCR formats (MSP; Herman et al. *Proc. Natl. Acad. Sci. USA* 93: 9821-9826, 1992), the hybridization is detected using a process comprising amplifying the bisulfite-treated DNA. Accordingly, by using one or more probe or primer that anneals specifically to the unmutated sequence under moderate and/or high stringency conditions an amplification product is only produced using a sample comprising a methylated nucleotide. Alternate assays that provide for selective amplification of either the methylated or the unmethylated component from a mixture of bisulfite-treated DNA are provided by Cottrell et al., *Nucl. Acids Res.* 32: e10, 2004 (HeavyMethyl PCR), Rand et al. *Nucl. Acids Res.* 33:e127. 2005 (Headloop PCR), Rand et al., *Epigenetics* 1:94-100, 2006 (Bisulfite Differential Denaturation PCR) and PCT/AU07/000389 (End-specific PCR).

Any amplification assay format described herein can be used, such as, for example, polymerase chain reaction (PCR), rolling circle amplification (RCA), inverse polymerase chain reaction (iPCR), in situ PCR (Singer-Sam et al., *Nucl. Acids Res.* 18:687, 1990), strand displacement amplification, or cycling probe technology. PCR techniques have been developed for detection of gene mutations (Kuppuswamy et al., *Proc. Natl. Acad. Sci. USA* 88:1143-1147, 1991) and quantitation of allelic-specific expression (Szabo and Mann, *Genes Dev.* 9:3097-3108, 1995; and Singer-Sam et al., *PCR Methods Appl.* 1: 160-163, 1992). Such techniques use internal primers, which anneal to a PCR-generated template and terminate immediately 5' of the single nucleotide to be assayed. Such as format is readily combined with ligase chain reaction as described herein above. The use of a real-time quantitative assay format is also useful. Subject to the selection of appropriate primers, such assay formats are generally described herein above and apply mutatis mutandis to the presently described selective mutagenesis approach.

Methylation-specific melting-curve analysis (essentially as described in Worm et al., *Clin. Chem.*, 47: 1183-1189, 2001) is also contemplated by the present invention. This process exploits the difference in melting temperature in amplification products produced using bisulfite treated methylated or unmethylated nucleic acid. In essence, non-discriminatory amplification of a bisulfite treated sample is performed in the presence of a fluorescent dye that specifically binds to double stranded DNA (e.g., SYBR Green I). By increasing the temperature of the amplification product while monitoring fluorescence the melting properties and thus the sequence of the amplification product is determined. A decrease in the fluorescence reflects melting of at least a domain in the amplification product. The temperature at which the fluorescence decreases is indicative of the nucleotide sequence of the amplified nucleic acid, thereby permitting the nucleotide at the site of one or more CpG dinucleotides to be determined. As the sequence of the nucleic acids amplified using the present invention The present invention also encompasses the use of real-time quantitative forms of PCR, such as, for example, TaqMan (Holland et al., *Proc. Natl. Acad. Sci. USA*, 88, 7276-7280, 1991; Lee et al., *Nucleic Acid Res.* 21, 3761-3766, 1993) to perform this embodiment. For example, the MethylLight method of Eads et al., *Nucl. Acids Res.* 28: E32, 2000 uses a modified TaqMan assay to detect methylation of a CpG dinucleotide. Essentially, this method comprises treating a nucleic acid sample with bisulfite and amplifying nucleic acid comprising one or more CpG dinucleotides that are methylated in a neoplastic cell and not in a control sample using an amplification reaction, e.g., PCR. The amplification reaction is performed in the presence of three oligonucleotides, a forward and reverse primer that flank the region of interest and a probe that hybridizes between the two primers to the site of the one or more methylated CpG dinucleotides. The probe is dual labelled with a 5' fluorescent reporter and a 3' quencher (or vice versa). When the probe is intact, the quencher dye absorbs the fluorescence of the reporter due to their proximity. Following annealing of to the PCR product the probe is cleaved by 5' to 3' exonuclease activity of, for example, Taq DNA polymerase. This cleavage releases the reporter from the quencher thereby resulting in an increased fluorescence signal that can be used to estimate the initial template methylation level. By using a probe or primer that selectively hybridizes to unmutated nucleic acid (i.e. methylated nucleic acid) the level of methylation is determined, e.g., using a standard curve.

Alternatively, rather than using a labelled probe that requires cleavage, a probe, such as, for example, a Molecular Beacon™ is used (see, for example, Mhlanga and Malmberg, *Methods* 25:463-471, 2001). Molecular beacons are single stranded nucleic acid molecules with a stem-and-loop structure. The loop structure is complementary to the region surrounding the one or more CpG dinucleotides that are methylated in a neoplastic sample and not in a control sample. The stem structure is formed by annealing two "arms" complementary to each other, which are on either side of the probe (loop). A fluorescent moiety is bound to one arm and a quenching moiety that suppresses any detectable fluorescence when the molecular beacon is not bound to a target sequence is bound to the other arm. Upon binding of the loop region to its target nucleic acid the arms are separated and fluorescence is detectable. However, even a single base mismatch significantly alters the level of fluorescence detected in a sample. Accordingly, the presence or absence of a particular base is determined by the level of fluorescence detected. Such an assay facilitates detection of one or more unmutated sites (i.e. methylated nucleotides) in a nucleic acid.

Fluorescently labelled locked nucleic acid (LNA) molecules or fluorescently labelled protein-nucleic acid (PNA) molecules are useful for the detection of nucleotide differences (e.g., as described in Simeonov and Nikiforov, *Nucleic Acids Research*, 30(17): 1-5, 2002). LNA and PNA molecules bind, with high affinity, to nucleic acid, in particular. DNA. Fluorophores (in particular, rhodomine or hexachlorofluorescein) conjugated to the LNA or PNA probe fluoresce at a significantly greater level upon hybridization of the probe to target nucleic acid. However, the level of increase of fluorescence is not enhanced to the same level when even a single nucleotide mismatch occurs. Accordingly, the degree of fluorescence detected in a sample is indicative of the presence of a mismatch between the LNA or PNA probe and the target nucleic acid, such as, in the presence of a mutated cytosine in a methylated CpG dinucleotide. Preferably, fluorescently labelled LNA or PNA technology is used to detect at least a single base change in a nucleic acid that has been previously amplified using, for example, an amplification method known in the art and/or described herein.

As will be apparent to the skilled artisan, LNA or PNA detection technology is amenable to a high-throughput detection of one or more markers by immobilizing an LNA or PNA probe to a solid support, as described in Orum et al., *Clin. Chem.* 45: 1898-1905, 1999.

Alternatively, a real-time assay, such as, for example, the so-called HeavyMethyl assay (Cottrell et al., *Nucl. Acids Res.* 32: e10, 2004) is used to determine the presence or level of methylation of nucleic acid in a test sample. Essentially, this method uses one or more non-extendible nucleic acid (e.g., oligonucleotide) blockers that bind to bisulfite-treated nucleic acid in a methylation specific manner (i.e., the blocker/s bind specifically to unmutated DNA under moderate to high stringency conditions). An amplification reaction is performed using one or more primers that may optionally be methylation specific but that flank the one or more blockers. In the presence of unmethylated nucleic acid (i.e., non-mutated DNA) the blocker/s bind and no PCR product is produced. Using a TaqMan assay essentially as described supra the level of methylation of nucleic acid in a sample is determined.

Other amplification based methods for detecting methylated nucleic acid following treatment with a compound that selectively mutates a non-methylated cytosine residue include, for example, methylation-specific single stranded conformation analysis (MS-SSCA) (Bianco et al., *Hum. Mutat.*, 14: 289-293, 1999), methylation-specific denaturing gradient gel electrophoresis (MS-DGGE) (Abrams and Stanton, *Methods Enzymol.*, 212: 71-74, 1992) and methylation-specific denaturing high-performance liquid chromatography (MS-DHPLC) (Deng et al, *Chin. J. Cancer Res.*, 12: 171-191, 2000). Each of these methods use different techniques for detecting nucleic acid differences in an amplification product based on differences in nucleotide sequence and/or secondary structure. Such methods are clearly contemplated by the present invention.

As with other amplification-based assay formats, the amplification product is analyzed using a range of procedures, including gel electrophoresis, gel filtration, mass spectrometry, and in the case of labelled primers, by identifying the label in the amplification product. In an alternative embodiment, restriction enzyme digestion of PCR products amplified from bisulfite-converted DNA is performed essentially as described by Sadri and Hornsby, *Nucl. Acids Res.* 24:5058-5059, 1996; and Xiong and Laird, *Nucl. Acids Res.* 25, 2532-2534, 1997), to analyze the product formed.

High throughput detection methods, such as, for example, matrix-assisted laser desorption/ionization time of flight (MALDI-TOF), electrospray ionization (ESI), Mass spectrometry (including tandem mass spectrometry, e.g. LC MS/MS), biosensor technology, evanescent fiber-optics technology or DNA chip technology, can also be employed.

As with the other assay formats described herein that utilize hybridization and/or amplification detection systems, combinations of such processes as described herein above are particularly contemplated the selective mutagenesis-based assay. In one example, the increased methylation is detected by performing a process comprising:

(i) treating the nucleic acid with an amount of a compound that selectively mutates a non-methylated cytosine residue under conditions sufficient to induce mutagenesis thereby producing a mutated nucleic acid;

(ii) hybridizing the nucleic acid to two non-overlapping and non-complementary primers each of which comprises a nucleotide sequence that is complementary to a sequence in the DNA comprising a methylated cytosine residue under conditions such that hybridization to the non-mutated nucleic acid occurs;

(iii) amplifying nucleic acid intervening the hybridized primers thereby producing a DNA fragment consisting of a sequence that comprises a primer sequence;

(iv) hybridizing the amplified DNA fragment to a probe comprising a nucleotide sequence that corresponds or is complementary to a sequence comprising a methylated cytosine residue under conditions such that hybridization to the non-mutated nucleic acid occurs; and (v) detecting the hybridization.

Negative Read-Out Assays

In another example, the assay format comprises a negative read-out system in which reduced methylation of DNA from a healthy/normal control sample is detected as a positive signal and preferably, methylated DNA from a neoplastic sample is not detected or is only weakly detected.

In a preferred embodiment, the reduced methylation is determined using a process comprising:

(i) treating the nucleic acid with an amount of a compound that selectively mutates a non-methylated cytosine residue under conditions sufficient to induce mutagenesis thereby producing a mutated nucleic acid;

(ii) hybridizing the nucleic acid to a probe or primer comprising a nucleotide sequence that is complementary to a sequence comprising the mutated cytosine residue under conditions such that selective hybridization to the mutated nucleic acid occurs; and (iii) detecting the selective hybridization.

In one embodiment of these examples, said cytosine residue is within a CpG dinucleotide or within a CpG island.

In this context, the term "selective hybridization" means that hybridization of a probe or primer to the mutated nucleic acid occurs at a higher frequency or rate, or has a higher maximum reaction velocity, than hybridization of the same probe or primer to the corresponding non-mutated sequence. Preferably, the probe or primer does not hybridize to the methylated sequence (or non-mutated sequence) under the reaction conditions used.

Hybridization-Based Assay Format

In one embodiment the hybridization is detected using Southern, dot blot, slot blot or other nucleic acid hybridization means (Kawai et. al., *Mol. Cell. Biol.* 14, 7421-7427, 1994; Gonzalgo et al., *Cancer Res.* 57, 594-599, 1997). Subject to appropriate probe selection, such assay formats are generally described herein above and apply mutatis mutandis to the presently described selective mutagenesis approach. Preferably, a ligase chain reaction format is employed to distinguish between a non-mutated and mutated nucleic acid. In this respect, the assay requirements and conditions are as described herein above for positive read-out assays and apply mutatis mutandis to the present format. However the selection of probes will differ. For negative read-out assays, one or more probes are selected that selectively hybridize to the mutated sequence rather than the non-mutated sequence.

Preferably, the ligase chain reaction probe(s) have 3'-terminal and/or 5'-terminal sequences that comprise a CpG dinucleotide that is not methylated in a healthy control sample, but is hypermethylated in cancer, such that the diagnostic probe and contiguous probe are capable of being ligated only when the cytosine of the CpG dinucleotide is mutated to thymidine e.g., in the case of a non-methylated cytosine residue.

As will be apparent to the skilled artisan the MSO method described supra is amenable to either or both positive and/or negative readout assays. This is because the assay described detects both mutated and non-mutated sequences thereby facilitating determining the level of methylation. However, an assay detecting only methylated or non-methylated sequences is contemplated by the invention.

Amplification-Based Assay Format

In an alternative example, the hybridization is detected using an amplification system using any amplification assay format as described herein above for positive read-out assay albeit using primers (and probes where applicable) selectively hybridize to a mutated nucleic acid.

In adapting the HeavyMethyl assay described supra to a negative read-out format, the blockers that bind to bisulfite-treated nucleic acid in a methylation specific manner bind specifically to mutated DNA under moderate to high stringency conditions. An amplification reaction is performed using one or more primers that may optionally be methylation specific (i.e. only bind to mutated nucleic acid) but that flank the one or more blockers. In the presence of methylated nucleic acid (i.e., mutated DNA) the blocker/s bind and no PCR product is produced.

In one example, the reduced methylation in the normal/healthy control subject is detected by performing a process comprising:
(i) treating the nucleic acid with an amount of a compound that selectively mutates non-methylated cytosine residues under conditions sufficient to induce mutagenesis thereby producing a mutated nucleic acid;
(ii) hybridizing the nucleic acid to two non-overlapping and non-complementary primers each of which comprises a nucleotide sequence that is complementary to a sequence in the DNA comprising a mutated cytosine residue under conditions such that hybridization to the mutated nucleic acid occurs;
(iii) amplifying nucleic acid intervening the hybridized primers thereby producing a DNA fragment consisting of a sequence that comprises a primer sequence;
(iv) hybridizing the amplified DNA fragment to a probe comprising a nucleotide sequence that corresponds or is complementary to a sequence comprising a mutated cytosine residue under conditions such that hybridization to the mutated nucleic acid occurs; and
(v) detecting the hybridization.

As will be apparent to the skilled artisan a negative read-out assay preferably includes a suitable control sample to ensure that the negative result is caused by methylated nucleic acid rather than a reaction failing.

In one particular embodiment, the increased methylation in a DNA region of the present invention is determined using a process comprising:
(i) treating the DNA derived from a biological sample with a compound that selectively mutates a non-methylated cytosine residue under conditions sufficient to induce mutagenesis;
(ii) amplifying the DNA of step (i) using primers designed to amplify a DNA region defined by one of SEQ ID NOs:1, 2, 3 or 4;
(iii) sequencing the amplification product of step (ii) to identify the presence in the DNA from said test sample of one or more cytosine residues which have not undergone mutation relative to the corresponding mutated residues in DNA from a control sample.

In another embodiment, said mutagenesis is induced with sodium bisulfite or equivalent agent and unmethylated cytosine residues are converted to uracil. These uracil residues are converted to thymine during the amplification step.

In accordance with the detection methods hereinbefore described, in one embodiment, where the DNA region which is analysed is the SEQ ID NO:1 region or substantially similar region, the sequence of the corresponding region isolated from a non-neoplastic control which has undergone a sodium bisulfite mutagenesis step would substantially correspond to SEQ ID NO:5 while the sequence of the corresponding region isolated from a subject exhibiting the onset or predisposition to the onset of a large intestine or breast neoplasm would substantially correspond to SEQ ID NO:6.

In accordance with this particular embodiment, the primers which are utilised correspond or are substantially similar to SEQ ID NOs: 18 and 19.

In yet another embodiment, where the DNA region which is analysed is the SEQ ID NO:2 region or substantially similar region, the sequence of the corresponding region isolated from a non-neoplastic control which has undergone a sodium bisulfite mutagenesis step would substantially correspond to SEQ ID NO:7 while the sequence of the corresponding region isolated from a subject exhibiting the onset or predisposition to the onset of a large intestine or breast neoplasm would substantially correspond to SEQ ID NO:8.

In accordance with this particular embodiment, the primers which are utilised correspond or are substantially similar to SEQ ID NOs:20 and 21.

In still another embodiment, where the DNA region which is analysed is the SEQ ID NO:3 region or substantially similar region, the sequence of the corresponding region isolated from a non-neoplastic control which has undergone a sodium bisulfite mutagenesis step would substantially correspond to SEQ ID NO:9 while the sequence of the corresponding region isolated from a subject exhibiting the onset or predisposition to the onset of a large intestine or breast neoplasm would substantially correspond to SEQ ID NO:10.

In accordance with this particular embodiment, the primers which are utilised correspond or are substantially similar to SEQ ID Nos:13 and 14. It should be appreciated by the person of skill in the art that where the primers are methylation specific primers, they will efficiently amplify the SEQ ID NO:10 molecule, which is not mutated, but will amplify very inefficiently the SEQ ID NO:9 molecule, which will have undergone mutation of the unmethylated cytosines. The same issue is relevant to SEQ ID NOs:11 and 12, respectively, discussed below.

In yet still another embodiment, where the DNA region which is analysed is the SEQ ID NO:4 region or substantially similar region, the sequence of the corresponding region isolated from a non-neoplastic control which has undergone a sodium bisulfite mutagenesis step would substantially correspond to SEQ ID NO: 11 while the sequence of the corresponding region isolated from a subject exhibiting the onset or predisposition to the onset of a large intestine neoplasm would substantially correspond to SEQ ID NO:12.

In accordance with this particular embodiment, the primers which are utilised correspond to SEQ ID NOs:13, 14 and 15.

As detailed hereinbefore, it would be appreciated by the person of skill in the art that variation between patient samples may occur in terms of the number of cytosine residues which are methylated. Accordingly, in the context of the embodiments hereinbefore recited, it should be understood that the sequences which are obtained subsequently to amplification may vary slightly from the sequences provided herein due to either allelic/polymorphic variations or differences in the actual number of cytosine residues which have undergone hypermethylation. Accordingly, these embodiments should be understood to extend to sequences exhibiting such variations. It is well within the skill of the person in the art to assess a DNA sequence to determine whether it is a naturally occurring variation of the DNA regions of the present invention.

This invention also provides kits for the detection and/or quantification of the diagnostic sequences of the invention, or expression or methylation thereof using the methods described herein.

For kits for detection of methylation, the kits of the invention can comprise at least one polynucleotide that hybridizes to at least one of the diagnostic sequences of the invention and at least one reagent for detection of gene methylation. Reagents for detection of methylation include, e.g., sodium bisulfite, polynucleotides designed to hybridize to sequence that is the product of a biomarker sequence of the invention if the biomarker sequence is not methylated (e.g., containing at least one C→U conversion), and/or a methylation-sensitive or methylation-dependent restriction enzyme. The kits may also include control natural or synthetic DNA sequences representing methylated or unmethylated forms of the sequence, such as those which are disclosed above in SEQ ID NOs:5-12. The kits can provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

As detailed hereinbefore, hypermethylation is associated with transcriptional silencing. Accordingly, in addition to the increased level of methylation of these genes providing a basis upon which to screen for the predisposition to or onset of a large intestine or breast neoplasm, the downregulation in the level of expression of these genes is also diagnostically valuable. In accordance with this aspect of the present invention, reference to a gene "expression product" or "expression of a gene" is a reference to either a transcription product (such as primary RNA or mRNA) or a translation product such as protein. In this regard, one can assess changes to the level of expression of a gene either by screening for changes to the level of expression product which is produced (i.e. RNA or protein), changes to the chromatin proteins with which the gene is associated, for example the presence of histone H3 methylated on lysine at amino acid position number 9 or 27 (repressive modifications) or changes to the DNA itself which acts to downregulate expression, such as changes to the methylation of the DNA.

Accordingly, another aspect of the present invention is directed to a method of screening for the onset or predisposition to the onset of a large intestine or breast neoplasm in an individual, said method comprising assessing the level of expression of the DNA region defined by Hg19 coordinates Chr6:163834295-163834500 in a biological sample from said individual wherein a lower level of expression of said DNA region relative to control levels is indicative of a neoplastic large intestine or breast cell or a cell predisposed to the onset of a neoplastic state.

The method of this aspect of the present invention is predicated on the comparison of the level of this neoplastic marker with the control levels of this marker. The "control level" may be either a "normal level", which is the level of marker expressed by a corresponding large intestine cell or cellular population which is not neoplastic.

As detailed hereinbefore, the normal (or "non-neoplastic") level may be determined using tissues derived from the same individual who is the subject of testing. However, it would be appreciated that this may be quite invasive for the individual concerned and it is therefore likely to be more convenient to analyse the test results relative to a standard result which reflects individual or collective results obtained from individuals other than the patient in issue.

Preferably, said control level is a non-neoplastic level.

As detailed hereinbefore, the present invention is designed to screen for a neoplastic cell or cellular population, which is located in the large intestine or breast. Accordingly, reference to "cell or cellular population" should be understood as a reference to an individual cell or a group of cells. Said group of cells may be a diffuse population of cells, a cell suspension, an encapsulated population of cells or a population of cells which take the form of tissue.

Reference to "expression" should be understood as a reference to the transcription and/or translation of a nucleic acid molecule. Reference to "RNA" should be understood to encompass reference to any form of RNA, such as primary RNA or mRNA or non-translated RNA (e.g. miRNAs etc.). Without limiting the present invention in any way, the modulation of gene transcription leading to increased or decreased RNA synthesis may also correlate with the translation of this RNA transcript (such as mRNA) to produce a protein product. Accordingly, the present invention also extends to detection methodology which is directed to screening for modulated levels or patterns of the marker protein product as an indicator of the neoplastic state of a cell or cellular population. Although one method is to screen for mRNA transcripts and/or the corresponding protein product, it should be understood that the present invention is not limited in this regard and extends to screening for any other form of expression product such as, for example, a primary RNA transcript.

In terms of screening for the downregulation of expression of a DNA region it would also be well known to the person of skill in the art that changes which are detectable at the DNA level are indicative of changes to gene expression activity and therefore changes to expression product levels. Such changes include but are not limited to, changes to DNA methylation. Accordingly, reference herein to "screening the level of expression" and comparison of these "levels of expression" to control "levels of expression" should be understood as a reference to assessing DNA factors which are related to transcription, such as gene/DNA methylation patterns. These have, in part, been described in detail hereinbefore.

It would also be known to a person skilled in the art that changes in the structure of chromatin are indicative of changes in gene expression. Silencing of gene expression is often associated with modification of chromatin proteins, methylation of lysines at either or both positions 9 and 27 of histone H3 being well studied examples, while active chromatin is marked by acetylation of lysine 9 of histone H3. Thus association of gene sequences with chromatin carrying repressive or active modifications can be used to make an assessment of the expression level of a gene.

Reference to "nucleic acid molecule" should be understood as a reference to both deoxyribonucleic acid molecules and ribonucleic acid molecules and fragments thereof. The present invention therefore extends to both directly screening for mRNA levels in a biological sample or screening for the complementary cDNA which has been reverse-transcribed from an mRNA population of interest. It is well within the skill of the person of skill in the art to design methodology directed to screening for either DNA or RNA. As detailed above, the method of the present invention also extends to screening for the protein product translated from the subject mRNA or the genomic DNA itself.

Although the preferred method is to detect the expression product or DNA changes of the neoplastic marker for the purpose of diagnosing neoplasia development or predisposition thereto, the detection of converse changes in the levels of said marker may be desired under certain circumstances, for example, to monitor the effectiveness of therapeutic or prophylactic treatment directed to modulating a neoplastic condition, such as adenoma or adenocarcinoma development. For example, where reduced expression of the subject marker indicates that an individual has developed a condition characterised by adenoma or adenocarcinoma development, for example, screening for an increase in the levels of this marker subsequently to the onset of a therapeutic regime may be utilised to indicate reversal or other form of improvement of the subject individual's condition. The method of the present invention is therefore useful as a one off test or as an on-going monitor of those individuals thought to be at risk of neoplasia development or as a monitor of the effectiveness of therapeutic or prophylactic treatment regimes directed to inhibiting or otherwise slowing neoplasia development.

Means of assessing the subject expressed neoplasm marker in a biological sample can be achieved by any suitable method, which would be well known to the person of skill in the art. To this end, it would be appreciated that to the extent that one is examining either a homogeneous cellular population (such as a tumour biopsy or a cellular population which has been enriched from a heterogeneous starting population) or a tissue section, one may utilise a wide range of techniques such as in situ hybridisation, assessment of expression profiles by microassays, immunoassays and the like (hereinafter described in more detail) to detect the absence of or downregulation of the level of expression of the marker of interest. However, to the extent that one is screening a heterogenous cellular population or a bodily fluid in which heterogeneous populations of cells are found, such as a blood sample, the absence of or reduction in level of expression of the marker may be undetectable due to the inherent expression of the marker by non-neoplastic cells which are present in the sample. That is, a decrease in the level of expression of a subgroup of cells may not be detectable. In this situation, a more appropriate mechanism of detecting a reduction in a neoplastic subpopulation of the expression level of the marker of the present invention is via indirect means, such as the detection of epigenetic changes.

Methods of detecting changes to gene expression levels (in addition to the methylation analyses hereinbefore described in detail), particularly where the subject biological sample is not contaminated with high numbers of non-neoplastic cells, include but are not limited to:
(i) In vivo detection.
  Molecular Imaging may be used following administration of imaging probes or reagents capable of disclosing altered expression of the markers in the intestinal tissues.
  Molecular imaging (Moore et al., *BBA*, 1402:239-249, 1988; Weissleder et al., *Nature Medicine* 6:351-355, 2000) is the in vivo imaging of molecular expression that correlates with the macro-features currently visualized using "classical" diagnostic imaging techniques such as X-Ray, computed tomography (CT), MRI, Positron Emission Tomography (PET) or endoscopy.
(ii) Detection of downregulation of RNA expression in the cells by Fluorescent In Situ Hybridization (FISH), or in extracts from the cells by technologies such as Quantitative Reverse Transcriptase Polymerase Chain Reaction (QRTPCR) or Flow cytometric qualification of competitive RT-PCR products (Wedemeyer et al., *Clinical Chemistry* 48:9 1398-1405, 2002).
(iii) Assessment of expression profiles of RNA, for example by array technologies (Alon et al., *Proc. Natl. Acad. Sci. USA:* 96, 6745-6750, June 1999).
(iv) Measurement of altered protein levels in cell extracts, for example by immunoassay. Testing for proteinaceous neoplastic marker expression product in a biological sample can be performed by any one of a number of suitable methods which are well known to those skilled in the art. Examples of suitable methods include, but are not limited to, antibody screening of tissue sections, biopsy specimens or bodily fluid samples. To the extent that antibody based methods of diagnosis are used, the presence of the marker protein may be determined in a number of ways such as by Western blotting. ELISA or flow cytometry procedures. These, of course, include both single-site and two-site or "sandwich" assays of the non-competitive types, as well Os in the traditional competitive binding assays. These assays also include direct binding of a labelled antibody to a target.
(v) Determining altered expression of a protein neoplastic marker on the cell surface, for example by immunohistochemistry.
(vi) Determining altered protein expression based on any suitable functional test, enzymatic test or immunological test in addition to those detailed in points (iv) and (v) above.

A person of ordinary skill in the art could determine, as a matter of routine procedure, the appropriateness of applying a given method to a particular type of biological sample.

Yet another aspect of the present invention is directed to an isolated nucleic acid molecule selected from the list consisting of:
(i) An isolated nucleic acid molecule or molecule complementary thereto or, fragment or derivative thereof comprising one or more of the nucleotide sequences, as set forth in any one of SEQ ID NO:5-12, or a nucleotide sequence having at least about 86%, 87%, 88%, 89%, 90%, 91%, 92%, 93%, 94%, 95%, 96%, 97%, 98% or 99% or more identity over the length of the sequence, or a nucleotide sequence capable of hybridising to said nucleic acid molecule or complementary form thereof under low stringency conditions; or
(ii) An isolated nucleic acid molecule or derivative or fragment thereof comprising one or more of the nucleotide sequences substantially as set forth in any one of SEQ ID NO:5-12 or a fragment of said molecule.

As detailed hereinbefore, SEQ ID NOs:5-12 represent the sequence of the DNA molecules which are expected to be obtained following bisulfite treatment and amplification of the DNA regions defined by SEQ ID NOs:1-4. Specifically, bisulfite treatment of DNA from large intestine neoplasias would be unlikely to result in cytosine to uracil mutagenesis events since only unmethylated cytosine residues undergo mutation. Several of the specific cytosine residues which undergo hypermethylation in a large intestine neoplasia have been identified in the context of SEQ ID NOs:1-4. Accordingly, amplification of the DNA regions defined by SEQ ID NOs:1, 2, 3 and 4, assuming that all the relevant cytosine residues are hypermethylated would be expected to result in a DNA product with a sequence substantially corresponding to SEQ ID NOs:6, 8, 10 and 12, respectively. In relation to DNA isolated from non-neoplastic cells, that is control DNA, mutagenesis of the relevant cytosine residues would be expected to occur following bisulfite treatment since the residues are unmethylated. Accordingly, amplification of the DNA regions defined by SEQ ID NOs:1, 2, 3 and 4 in this situation would be expected to result in a DNA product with a sequence substantially corresponding to SEQ ID NOs:5, 7, 9 and 11, respectively. It would be appreciated by the person of skill in the art, and as detailed hereinbefore, that variation in the extent of hypermethylation, both in terms of its degree and the number of cytosine residues which are hypermethylated, can occur between different patients. Nevertheless, despite that fact that each neoplastic sample may not exhibit precisely identical hypermethylation patterns, the fact remains that a neoplastic sample will exhibit detectable hypermethylation in the regions defined by SEQ ID NOs:1-4 relative to non-neoplastic samples.

From the point of view of electing specifically to assess hypermethylation via a cytosine to uracil mutagenesis method, followed by amplification of the DNA region in issue, the methylated and unmethylated sequences defined by SEQ ID NOs:5-12 provide the standard against which patient results from this diagnostic method can be assessed. It is irrelevant whether the test samples exhibit hypermethylation to the full extent represented by SEQ ID NOs:6, 8, 10 and 12. Rather, provided that the sample exhibits hypermethylation at a higher level to that represented by SEQ ID NOs:5, 7, 9 and 11, the result will be indicative that the patient from whom the sample was taken has a large intestine neoplasm. SEQ ID NOs:5, 7, 9, 11 and SEQ ID NOs:6, 8, 10, 12 therefore become the standards against which test results can be analysed. Any increase in methylation will be clearly evident against SEQ ID NOs:5, 7, 9 and 11 and is indicative of a neoplasm. Comparing the degree and pattern of hypermethylation to the sequences defined by SEQ ID NOs:6, 8, 10 and 12 provides useful information in relation to variability which may exist between individual patients or cohorts in terms of hypermethylation patterns. Accordingly, inclusion of one or more of these standard sequences in diagnostic kits is contemplated.

The phrases "nucleic acid" or "nucleic acid sequence" as used herein refer to an oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) *Toxicol. Appl. Pharmacol.* 144:189-197; Strauss-Soukup et al. (1997) *Biochemistry* 36:8692-8698; Samstag et al. (1996) *Antisense Nucleic Acid Drug Dev* 6:153-156.

To this end, it should be understood that the present invention extends to antisense nucleic acid molecules, siRNA and miRNA which are directed to the nucleic acid molecules hereinbefore defined.

The present invention should also be understood to extend to probes and primers directed to the nucleic acid molecules hereinbefore defined.

It would be appreciated that the design of antisense nucleic acid molecules and probes and primers would be a matter of routine procedure to the person of skill in the art in light of the detailed teachings provided herein. Said antisense molecules, probes and primers are preferably specific for their target molecule although it would be appreciated that the same cross-reactivity may occur depending on the sequence and length of the antisense molecule, probe or primer. Whether or not a level of cross-reactivity/promiscuity is acceptable is a judgement to be made by the skilled person and will depend on the particularities of the situation. In general, increased specificity can be effected by increasing the length of the probe or primer. Preferably, said probe or primer comprises a sequence of nucleotides of at least 10, 20, 30, 40 or 50 nucleotides, although the use of larger molecules are also contemplated, derived from or directed to the nucleotide sequences hereinbefore defined. This sequence may be labelled with a reporter molecule capable of giving an identifiable signal.

The nucleic acid molecule of the present invention is preferably in isolated form or ligated to a vector, such as an expression vector. By "isolated" is meant a nucleic acid molecule having undergone at least one purification step and this is conveniently defined, for example, by a composition comprising at least about 10% subject nucleic acid molecule, preferably at least about 20%, more preferably at least about 30%, still more preferably at least about 40-50%, even still more preferably at least about 60-70%, yet even still more preferably 80-90% or greater of subject nucleic acid molecule relative to other components as determined by molecular weight, sequence or other convenient means. The nucleic acid molecule of the present invention may also be considered, in a preferred embodiment, to be biologically pure.

The nucleic acids of the invention can be made, isolated and/or manipulated by, e.g., cloning and expression of cDNA libraries, amplification of mRNA or genomic DNA by PCR, and the like.

The nucleic acids of this invention, whether RNA, iRNA, antisense nucleic acid, cDNA, genomic DNA, vectors, viruses or hybrids thereof, may be isolated from a variety of sources, genetically engineered, amplified, and/or expressed or generated recombinantly.

Alternatively, these nucleic acids can be synthesized in vitro by well-known chemical synthesis techniques, as described in, e.g., Adams (1983) *J. Am. Chem. Soc.* 105:661; Belousov et al. (1997) supra; Frenkel et al. (1995) supra; Blommers et al. (1994) supra; Narang et al. (1979) *Meth. Enzymol.* 68:90; Brown et al. (1979) *Meth. Enzymol.* 68:109; Beaucage (1981) *Tetra. Lett.* 22:1859; U.S. Pat. No. 4,458, 066.

Techniques for the manipulation of nucleic acids, such as, e.g., subcloning, labelling probes (e.g., random-primer labelling using Klenow polymerase, nick translation, amplification), sequencing, hybridization and the like are well described in the scientific and patent literature.

Nucleic acids, vectors, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabelling, scintillation counting, and affinity chromatography.

The invention provides cloning vehicles comprising nucleic acids of the invention. Cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, *Aspergillus* and yeast). Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods. Methods for cloning in vitro amplified nucleic acids are described, e.g., U.S. Pat. No. 5,426,039. To facilitate cloning of amplified sequences, restriction enzyme sites can be "built into" a PCR primer pair.

The terms "similarity" and "identity" as used herein include exact identity between compared sequences at the nucleotide level. Where there is non-identity at the nucleotide level, "similarity" and include "identity" differences between sequences which may encode different amino acids that are nevertheless related to each other at the structural, functional, biochemical and/or conformational levels. In a particularly preferred embodiment, nucleotide sequence comparisons are made at the level of identity rather than similarity.

Terms used to describe sequence relationships between two or more polynucleotides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (*Nucl. Acids Res.* 25, 3389, 1997). A detailed discussion of sequence analysis can be found in Unit 19.3 of Ausubel et al. ("Current Protocols in Molecular Biology" John Wiley & Sons Inc, Chapter 15, 1994-1998). A range of other algorithms may be used to compare the nucleotide sequences such as but not limited to PILEUP, CLUSTALW, SEQUENCER or VectorNTI.

The terms "sequence similarity" and "sequence identity" as used herein refers to the extent that sequences are identical or functionally or structurally similar on a nucleotide-by-nucleotide basis over a window of comparison. Thus, a "percentage of sequence identity", for example, is calculated by comparing two optimally aligned sequences over the window of comparison, determining the number of positions at which the identical nucleic acid base (e.g. A, T, C, G) occurs in both sequences to yield the number of matched positions, dividing the number of matched positions by the total number of positions in the window of comparison (i.e., the window size), and multiplying the result by 100 to yield the percentage of sequence identity.

The phrases "substantially identical" or "substantially similar" in the context of two nucleic acids, can refer to two or more sequences that have, e.g., at least about 86%, 87%, 88%, 89%, 90%, 91%, 92%, 93%, 94%, 95%, 96%, 97%, 98%, 99% or more sequence identity, when compared and aligned for maximum correspondence.

The invention provides isolated or recombinant nucleic acids that hybridize under low stringency conditions to an exemplary sequence of the invention. In alternative aspects, the stringent conditions are highly stringent conditions or medium stringent conditions, as known in the art and as described herein. These methods may be used to isolate nucleic acids of the invention.

"Hybridization" refers to the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C) % (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *Eur. J. Biochem.* 46: 83, 1974). Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

Where nucleic acids of the invention are defined by their ability to hybridize under high stringency, these conditions comprise about 50% formamide at about 37° C. to 42° C. In one aspect, nucleic acids of the invention are defined by their ability to hybridize under reduced stringency comprising conditions in about 35% to 25% formamide at about 30° C. to 35° C. Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

Another aspect of the present invention provides a diagnostic kit for assaying biological samples comprising one or more agent for detecting the marker of the present invention and reagents useful for facilitating the detection by said agents. Further means may also be included, for example, to receive a biological sample. The agent may be any suitable detecting molecule.

In one embodiment, said kit comprises one or more nucleic acid molecules corresponding to SEQ ID NOs:5, 6, 7, 8, 9, 10, 11 or 12, or substantially similar nucleic acid molecule. As detailed hereinbefore, these sequences are useful as the standards (controls) against which the product amplified from the test sample is assessed.

In another embodiment, said kit comprises one or more amplification primer sets which primer sets correspond to the sequences as follows:
(i) SEQ ID NOs:13 and 14 or substantially similar sequences;
(ii) SEQ ID Nos:13, 14 and 15 or substantially similar sequences;
(iii) SEQ ID NOs:18 and 19 or substantially similar sequences;
(iv) SEQ ID NOs:20 and 21 or substantially similar sequences.

The present invention is further described by reference to the following non-limiting examples.

Example 1

Identification of Putative Region of Differential DNA Methylation

Genome-wide analysis of DNA methylation using the Bisulfite-tag procedure described in International Patent Publication No. WO2011/017760 was applied to three colorectal cancer cell lines, HCT116, SW480 and LIM in comparison with DNA from peripheral blood. This technique characterises the level of DNA methylation at TaqI (TCGA) and MspI (CCGG) restriction sites. Among the differentially methylated sites identified was a CpG site within a TaqI restriction site located on Chromosome 6, position 163,834,406. This site also showed differential methylation in comparison to samples of 8 colorectal cancer DNAs with their 8 matched normal tissue DNAs. This site was identified to lie within the previously uncharacterised gene Refseq LOC100526820 and DNA methylation in this and surrounding sequence was investigated as described hereafter. The gene has subsequently been named CAHM (colorectal adenocarcinoma hypermethylated).

Example 2

Methylation of Cytosines in SEQ ID NO:1 in Colorectal Tissue Specimens from 10 Normal Tissue Specimens and 10 Colorectal Cancer Specimens Primers were designed to amplify two regions of the LOC 100526820 gene after chemical conversion with sodium bisulfite. Reaction with sodium bisulfite converts cytosine to uracil (subsequently amplified as thymine) while leaving 5-methyl cytosine unconverted; primers were designed to equivalently amplify methylated and unmethylated DNA sequences.

```
Forward primer:
                                      (SEQ ID NO: 18)
5'ATTTGTAAAAATGTTGATTTTTGTTTTTTAGAT Reverse primer:
                                      (SEQ ID NO: 19)
5'TCTTATTACACCTTCCCRTTATTCTA
```

The primers were used for PCR from bisulfite treated DNA of 10 colorectal cancer specimens, their matched normal tissue and normal blood DNA. Amplification was done using Promega GoTaq master mix (without Sybr-Green), 3 mM MgCl$_2$ and with primers at 200 nM and 10 ng of input DNA. Cycling conditions were 95° C., 2 min (1 cycle, followed by 50 cycles of 95° C. 15 sec, 56° C. 30 sec; 72° C. 30 sec. Amplified bands of DNA were gel purified and ligated with linkers for sequencing on the Roche 454 Titanium FLX system. Samples from individual patients and the blood DNA sample were separately ligated with bar coded "MID" linkers (Roche Cat No 05619211001) so that sequence reads could be assigned to individual samples for sequence alignment and scoring. Libraries of this, SEQ ID NO:2, Example 3 below, and amplicons from other genes were prepared following protocols provided with the Roche Library preparation kit and reagents and sequenced on two halves of a flow cell; one half contained all the cancer samples and one the equivalently bar-coded normal samples. The bisulfite sequencing reads were segregated to individual samples using the bar-code sequences and aligned with the bisulfite converted sequence, SEQ ID NO:6. After best alignment, the fraction of cytosines at each potential CpG methylation site (sites labelled 36, 38, 63 etc in FIG. 1, with reference to nucleotide position in the amplicon) was determined for each sample.

FIG. 1(b) shows the profile of methylation at each of the CpG sites within the amplicon. The solid lines represent cancer samples and the corresponding dashed lines show the methylation status of the matched normal tissue DNA. It is evident that 7 of the cancer samples show high levels of methylation (around 80%) at most CpG sites, two show intermediate levels and one shows minimal methylation. By contrast, 8 of 10 normal DNA samples show methylation, generally at <10% across the amplicon, one at low levels, 10-20% and one at intermediate levels, about 30%. The corresponding cancer sample for this partially methylated normal sample is one of those showing high level methylation. Significantly, analysis of DNA derived from peripheral blood showed minimal methylation (<3%) at all CpG sites across the amplicon. Thus the level of methylation at CpG sites within SEQ ID NO:1, distinguishes colorectal cancer DNA from that of matched normal colon tissue and control DNA derived from blood.

Example 3

Methylation of Cytosines in SEQ ID NO:2 in Colorectal Tissue Specimens from 10 Normal Tissue Specimens and 10 Colorectal Cancer Specimens An adjacent region SEQ ID NO:2 shown in FIG. 2(a), was analysed as for SEQ ID NO:1 using the primer pair:

```
Forward primer:
                                  (SEQ ID NO: 20)
5'GTYGTGTTGTTTTTTAGTTTTTTAGTAAATT Reverse primer:
                                  (SEQ ID NO: 21)
5'CACRATACRAAAAACTAATAAACTTTCCTTA
```

FIG. 2(b) shows the profile of methylation at each of the CpG sites within the amplicon. The solid lines represent cancer samples and the corresponding dashed lines show the methylation status of the matched normal tissue DNA. The sequence characteristics of the central region of the amplicon limited read length in the Roche 454 sequencing system; thus only CpG sites proximal to the starting end of the sequence read could be assessed. Nevertheless, it is clear that cancer-specific hypermethylation includes the first 6 CpG sites (to base 61, Chromosome co-ordinates 163,834, 653 to 163,834,6681) at the left end of the amplicon and extends to include the last 10 CpG sites, between bases 195 and 252 (Chromosome co-ordinates 163,834,815 to 163, 834,872). Again 9 of 10 cancer samples show intermediate or high levels of methylation and only one matched normal sample shows any significant methylation. Additionally, CpG site methylation within this amplicon was also very low in peripheral blood DNA (<3%). The combined data indicate that the region encompassed by the two sequenced amplicons, ie from base 163834295 to 163834906 of Chromosome 6 (hg19 sequence) demonstrates colorectal cancer-specific hypermethylation and is suitable for the development of assays for detection of colorectal cancer.

Example 4

Measurement of Methylation Levels in the CAHM Gene (LOC100526820) in Colon Tissue Specimens Using a Methylation Specific qPCR Assay for Amplification DNA was extracted from colon tissue specimens comprising 10 adenomas, 15 Stage 1, 18 Stage B, 28 Stage C, 7 Stage IV, 6 matched normal colon specimens and 7 other normal colon tissue. Isolated DNA was bisulfite converted using the Zymo EZ Gold bisulfite conversion kit as recommended by manufacturer.

The PCR assay is a 15 uL reaction mixture containing a final concentration of 1× Platinum TaqDNA polymerase (Invitrogen), 3 mM MgCl2, 200 nM of oligonucleotide SEQ ID NOs:13 and 14, 200 uM dNTPs (New England BioLabs), 1× Platinum Buffer and 1:120,000 dilution of Molecular Probe SYBR Green (Invitrogen). Cycling conditions are 95° C. for 2 min, followed by three cycles of 92° C., 15 sec; 62° C. 15 sec and 72° C. 20 sec. This was followed by 50 cycles of 82° C., 15 sec, 63° C. 15 sec and 72° C. 20 sec. The PCR amplifications were performed in a Roche LightCycler 480 real-time PCR instrument using 384-well plates.

Levels of methylation were quantified using a standard curve of fully methylated DNA, 40 pg to 5 ng mixed with peripheral blood leukocyte DNA to give a total input of 5 ng. Table 1 summarises the frequency of methylation of LOC 100526820 SEQ ID NO:3. The PCR-targeted SEQ ID NO:10 was found to be positive in 70% of the tissue DNA extracted from adenomas, 74% positive in the collective cancer tissue specimens but only methylated in 25% of the tested normal colorectal tissue specimens (and here at low levels).

Example 5

Detection of Colorectal Neoplasia by Measuring Methylation Levels in the CAHM Gene (LOC100526820) in Free Circulating Plasma DNA from 25 Colonoscopy Negative Healthy Normals, 25 Patients with Colorectal Adenomas and 25 Patients with Colorectal Cancer DNA was extracted 4 mL of human blood plasma from 25 patients with colorectal adenomas, 25 patients with colorectal cancer and 25 colonoscopy negative healthy patients. The extraction was performed using the QIAmp Isolation of free circulating nucleic acids from serum/plasma (QIAGEN). Isolated DNA was bisulfite converted using the Zymo bisulfite conversion kit as recommended by manufacturer. A total of 36 uL of bisulfite converted DNA was retrieved from 4 mL of plasma. A total of 2.5 uL of bisulfite converted DNA from each patient was used in a $1^{st}$ round PCR reaction of 30 uL consisting of a final concentration of Ix Platinum TaqDNA polymerase (Invitrogen), 3.3 mM MgCl2, 200 nM of oligonucleotide SEQ ID NOs:13 and 15, 200 uM dNTPs (New England BioLabs) and 1× Platinum Buffer. Cycling conditions were 95° C. for 2 min, followed by eleven cycles of 92° C., 15 sec; 60° C., 30 sec and 72° C. 30 sec. The PCR amplifications were performed in PALM end-point PCR cycler using 96-well plates. A second PCR was performed on 1 uL of material from PCR round 1 into a total PCR reaction of 15 uL consisting of a final concentration of 1× Platinum TaqDNA polymerase (Invitrogen), 4 mM MgCl2, 200 nM of oligonucleotide SEQ ID NOs:13 and 14, 200 uM dNTPs (New England BioLabs), 1× Platinum Buffer and 1:120,000 dilution of Molecular Probe SYBR Green (Invitrogen). Cycling conditions are 95° C. for 2 min, followed by three cycles of 92° C., 15 sec; 62° C. 15 sec and 72° C. 20 sec. This was followed by 47 cycles of 82° C., 15 sec, 62° C. 15 sec and 72° C. 20 sec. A melt curve analysis was performed at 95° C., 5 sec, 65° C. 1 min and a continuous increase to 97° C. using a ramp speed of 0.11° C./sec. The PCR amplifications were performed in a Roche LightCycler 480 real-time PCR instrument using 384-well plates. Patient samples with product melting curves at 77.4° C.+/−0.5° C. were called positive. Levels of methylation were quantified using a standard curve of fully methylated DNA, 40 pg to 5 ng mixed with peripheral blood leukocyte DNA to give a total input of 5 ng. Table 2 summarises the frequency of methylation of the CAHM gene (LOC100526820) in free circulating plasma DNA.

The sensitivity of detection is seen to increase with increasing stage of the cancer. These data demonstrate the potential utility of specific assays for methylation of the LOC100526820 in DNA isolated from plasma for detection of colorectal neoplasia.

Example 6

Measurement of Methylation Levels in CAHM (LOC100526820) in Colon Breast, Prostate and Lung Tissue Specimens Using a Methylation Specific qPCR Assay for Amplification DNA was extracted from tissue specimens comprising 10 breast cancer and 10 matched normal breast tissue specimens, 10 lung cancer and 10 matched normal lung tissue specimens and 5 prostate cancer and 5 matched normal prostate tissue specimens. In addition, a previously untested cohort of 10 colorectal cancer tissue specimens and 10 matched normal colon tissue specimens were included as controls. The concentration of isolated DNA was determined using 200 nM of CFF1 primers and cycling conditions described in Devos et al. *Clin Chem* 2009; 55:1337-1346 in a modified 15 µL PCR mixture comprising: 0.05 U/µL Platinum Taq DNA polymerase (Invitrogen), 1× Platinum Buffer, 3 mM $MgCl_2$, 200 µM dNTPs and 200 nM of a TaqMan probe (5'-6FAM-ATG GAT GAA GAA AGA AAG GAT GAGT-BHQ-1) (SEQ ID NO:22).

1 µg DNA was bisulphite converted using the Epitect Plus Bisulfite kit as recommended by manufacturer (QIAGEN). The concentration of purified bisulphite converted DNA was determined using bisulphite conversion specific ACTB primers (Forward primer: 5'-GTG ATG GAG GAG GTT TAG TAA GTT (SEQ ID NO:23); Reverse primer: 5'-AAT TAC AAA AAC CAC AAC CTA ATA AA) (SEQ ID NO:24) in a final concentration of 900 nM for each primer in a 15 L PCR comprising 0.05 U/µL Platinum Taq DNA polymerase (Invitrogen), 1× Platinum Buffer, 2 mM MgCl2, 200 µM dNTPs (Invitrogen) and 100 nM TaqMan probe (5'-6FAM-ACC ACC ACC CAA CAC ACA ATA ACA AAC ACA-BHQ-1) (SEQ ID NO:25). PCR cycling conditions: 95° C., 2 minutes; 60 cycles of [95° C., 10 seconds; 60° C., 50 seconds], 4° C. 10 seconds.

The level of CAHM methylation in 5 ng bisulphite converted tissue DNA (triplicates) was determined using the CAHM PCR assay in a 25 µL reaction mixture containing a final concentration of 1× Platinum TaqDNA polymerase (Invitrogen), 3 mM MgCl2, 200 nM of oligonucleotide SEQ ID NOs:13 and 14, 200 µM dNTPs, 1× Platinum Buffer and 1:120,000 dilution of Molecular Probe SYBR Green (Invitrogen). PCR cycling conditions: 95° C. 2 min, 3 cycles of [92° C., 15 seconds; 62° C., 15 seconds; 72° C., 20 seconds] followed by 50 cycles of [82° C., 15 seconds; 63° C., 15 seconds; 72° C., 20 seconds] where after a melt curve analysis was performed with the settings of 95° C., 5 sec, 65° C., 1 min, ramping to 97° C. at 0.11° C./sec continuous acquisition (5/sec); followed by cooling to 40° C. for 10 seconds. The PCR amplifications were performed in a Roche LightCycler 480 real-time PCR instrument using 96-well plates.

Levels of methylation were quantified using a standard curve of fully methylated DNA, 20 pg to 5 ng. Table 3 summarises the frequency of methylation of CAHM (LOC100526820) SEQ ID NO:3.

The PCR-targeted SEQ ID NO:10 was more than 2% methylated in 9 of 10 colorectal cancer specimens and 1 of 10 normal specimens. In contrast, CAHM showed no methylation in any of the 10 paired prostate specimens. Low level methylation (less than 0.3%) was measured in 3 of the 20 matched lung specimens (2 normals and 1 cancer) and 18 of the matched breast specimens. Only 2 breast cancer specimens had more than 2% CAHM methylation. These data demonstrate the high sensitivity of methylation in the CAHM locus for detection of colon cancer compared with other cancers, but also that a CAHM methylation may detect a sub-group of breast cancers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

| | | SEQ ID NO: 10 | |
| --- | --- | --- | --- |
| | Total samples | Number positive (2% cut-off) | % positive |
| Adenoma | 10 | 7 | 70 |
| Cancer A | 15 | 8 | 53 |
| Cancer B | 18 | 13 | 72 |
| Cancer C | 28 | 22 | 79 |
| Cancer D | 7 | 7 | 100 |
| Cancer Total | 68 | 50 | 74 |
| Matched normal | 6 | 1 | 16 |
| Other normal colon | 7 | 2 | 28 |
| Sm Int; stomach; rectum | 3 | 1 | Sm int. |

TABLE 2

| 75 | n (%) | Average | F/M | % pos |
| --- | --- | --- | --- | --- |
| Normal | 25 | 59.9 | 12/13 | 8% |
| Adenoma | 25 | 59.2 | 14/11 | 8% |
| LGD | — | — | — | — |
| HGD | — | — | — | — |
| >3 lesions | 7 | 59.4 | 3/4 | 14% |
| <3 lesions | 18 | 59.1 | 11/7 | 6% |
| TA | 15 | 59.3 | 8/7 | 0% |
| TVA | 0 | — | — | — |
| VA | 4 | 59 | 3/1 | 25% |
| other | 6 | 59.2 | 3/3 | 17% |
| >10 mm | — | — | — | — |
| <10 mm | 25 | 59.2 | 14/11 | 8% |
| Cancer | 25 | 61.1 | 14/11 | 64% |
| I | — | — | — | — |
| II | 9 | 63 | 6/3 | 33% |
| III | 8 | 64.6 | 4/4 | 63% |
| IV | 8 | 55.4 | 4/4 | 100% |
| Stage unk | — | — | — | — |

TABLE 3

| | | SEQ ID NO: 10 | |
| --- | --- | --- | --- |
| | Total samples | Number positive (2% cut-off) | % positive |
| Breast cancer | 10 | 2 | 20 |
| Matched normal breast tissue | 10 | 0 | 0 |
| Lung cancer | 10 | 0 | |
| Matched normal lung tissue | 10 | 0 | 0 |
| Prostate cancer | 5 | 0 | 0 |
| Matched normal prostate tissue | 5 | 0 | 0 |
| Colon cancer | 10 | 9 | 90 |
| Matched normal prostate tissue | 10 | 1 | 10 |

BIBLIOGRAPHY

Abrams and Stanton, *Methods Enzymol.*, 212: 71-74, 1992
Adams (1983) *J. Am. Chem. Soc.* 105:661
Alon et al., *Proc. Natl. Acad. Sci. USA:* 96, 6745-6750, June 1999
Altschul et al. (*Nucl. Acids Res.* 25: 3389, 1997
Ammerpohl et al. *Biochim Biophys Acta.* 1790:847-62, 2009
Ausubel, F. et al., "Current Protocols in Molecular Biology", John Wiley & Sons, (1998)
Beaucage, et al. *Tetrahedron Letters* 22: 1859-1862, 1981
Belousov et al. (1997) *Nucleotide. Acids Res.* 25(17):3440-3444
Blommers et al. (1994) *Biochemistry* 33:7886-96
Bonner and Laskey, *Eur. J. Biochem.* 46: 83, 1974
Breslauer et al., *Proc. Natl. Acad. Sci. USA*, 83: 3746-3750, 1986
Brown et al. (1979) *Meth. Enzymol.* 68:109
Caruthers, M. H., et al., "Methods in Enzymology," Vol. 154, pp. 287-314 (1988)
Chen and Kwok, *Nucleic Acids Res.* 25: 347-353, 1997
Clark et al. *Nat Protoc.* 1:2353-64, 2006
Cottrell et al., *Nucl. Acids Res.* 32: e10, 2004
DeGraves, et al., *Biotechniques* 34(1):106-10, 112-5 (2003)
Deiman B, et al., *Mol. Biotechnol.* 20(2):163-79 (2002)
Deng et al, *Chin. J. Cancer Res.*, 12: 171-191, 2000
Devos et al. *Clin Chem* 2009; 55:1337-1346
Dieffenbach and Dveksler (Eds) (In: PCR Primer: A Laboratory Manual, Cold Spring Harbor Laboratories, NY, 1995
Eads et al., *Cancer Res.* 59:2302-2306 (1999)
Egholm et al., *Am. Chem. Soc.*, 114: 1895, 1992
Egholm et al., *Nature*, 365: 566, 1993
Frenkel et al. (1995) *Free Rad. Biol. & Med.* 19(3):373-380
Frommer et al., *Proc. Natl. Acad. Sci. USA* 89:1827-1831 (1992)
Gibson et al., *Genome Research* 6:995-1001 (1996)
Golub et al., *Science*, 286:531-537, 1999
Gonzalgo & Jones, *Nucleic Acids Res.* 25:2529-2531 (1997)
Gonzalgo et al., *Cancer Res.* 57, 594-599, 1997
Herman et al., *Proc. Natl. Acad. Sci. USA* 93:9821-9826, (1996)
Holland et al., *Proc. Natl. Acad. Sci. USA*, 88, 7276-7280, 1991 http://www.sciencedaily.com/releases/2010/04/100419150831.htm
Kawai et al., *Mol. Cell. Biol.* 14:7421-7427, 1994
Kristensen and Hansen, *Clin Chem.* 55:1471-83, 2009
Kuppuswamy et al., *Proc. Natl. Acad. Sci. USA* 88:1143-1147, 1991
Landegren et al., *Genome Res.*, 8(8): 769-776, 1998
Lee et al., *Nucleic Acid Res.* 21, 3761-3766, 1993
Markowitz S D, Bertagnolli M M (December 2009). "Molecular basis of colorectal cancer". *N. Engl. J. Med.* 361 (25): 2449-60
Marmur and Doty, *J. Mol. Biol.* 5: 109, 1962
Mata (1997) *Toxicol. Appl. Pharmacol.* 144:189-197
Messing, *Methods Enzymol*, 101, 20-78, 1983
Mhlanga and Malmberg, *Methods* 25:463-471, 2001
Moore et al., *BBA*, 1402:239-249, 1988
Narang, et al. *Meth. Enzymol* 68: 90, 1979
Nielsen et al., *J. Chem. Soc. Perkin Trans.*, 1:3423, 1997
Olek, et al. *Nat. Genet.* 17(3): 275-6 (1997)
Orum et al., *Clin. Chem.* 45: 1898-1905, 1999
Orum et al., *Nucl. Acids Res.*, 21: 5332, 1993
PCT Publication No. WO 00/70090
Rand et al. *Nucl. Acids Res.* 33:e127, 2005
Rand et al., *Epigenetics* 1:94-100, 2006
Rein, et al. *Nucleic Acids Res.* 26 (10): 2255-64 (1998)
Robinson et al. *Epigenomics* 2:587-98 (2010)
Sadri & Hornsby, *Nucl. Acids Res.* 24:5058-5059 (1996)
Sambroock et al. Molecular Cloning, A Laboratory Manual (2nd Ed., CSHP, New York 1989) (Cold Spring Harbour Laboratory Press, 1989)
Samstag et al. (1996) *Antisense Nucleic Acid Drug Dev* 6:153-156
Santa Lucia, *Proc. Natl. Acad. Sci. USA*, 95: 1460-1465, 1995
Shames et al. *Cancer Lett.* 251:187-98, 2007
Simeonov and Nikiforov, *Nucleic Acids Research*, 30(17): 1-5, 2002
Singer-Sam et al., *Nucl. Acids Res.* 18:687, 1990
Singer-Sam et al., *PCR Methods Appl.* 1: 160-163, 1992
Singh and Wengel, *Chem. Commun.* 1247, 1998
Southern et al., *Genomics*, 13: 1008-1017, 1992
Strauss-Soukup et al. (1997) *Biochemistry* 36:8692-8698
Szabo and Mann, *Genes Dev.* 9:3097-3108, 1995
Toyota et al., *Cancer Res.* 59:2307-12 (1999)
U.S. Pat. No. 5,786,146
U.S. Patent Publication 2005/0069879
Uhlmann et al., *Electrophoresis*, 23: 4072-4079, 2002
Wedemeyer et al., *Clinical Chemistry* 48:9 1398-1405, 2002
Weissleder et al., *Nature Medicine* 6:351-355, 2000
Weitzel J N (December 1999). "Genetic cancer risk assessment. Putting it all together". *Cancer* 86 (11 Suppl): 2483-92.
Xiong & Laird, *Nucleic Acids Res.* 25:2532-2534 (1997)
Zyskind et al., Recombinant DNA Laboratory Manual, (Acad. Press, 1988)

The invention claimed is:

1. A method for detecting the onset, or predisposition to the onset, of a large intestine neoplasm in a human subject, said method comprising:
   assessing the methylation level of CpG dinucleotides in SEQ ID NO: 1 and/or the complement thereof in a free circulating plasma DNA sample from said subject;
   wherein said assessing comprises obtaining DNA from the sample, bisulfate conversion of the obtained DNA, and amplification of converted SEQ ID NO: 1 and/or the complement thereof with primers SEQ ID NO: 18 and 19;
   comparing the assessed methylation level to a methylation level of CpG dinucleotides in SEQ ID NO: 1 and/or the complement thereof in a large intestine tissue sample or free circulating plasma DNA sample from a human subject that does not have a large intestine neoplasm;
   detecting a higher level of CpG methylation in the assessed methylation level as compared to the methylation level of CpG dinucleotides in SEQ ID NO: 1 and/or the complement thereof in a large intestine tissue sample or free circulating plasma DNA from a human subject that does not have a large intestine neoplasm; and
   correlating the higher level of CpG methylation in the assessed methylation status with the onset, or predisposition to the onset, of a large intestine neoplasm in the subject.

2. The method according to claim 1, wherein assessing the methylation level of CpG dinucleotides in SEQ ID NO: 1 and/or the complement thereof comprises:
   (i) methylation-specific PCR;
   (ii) the MethyLight assay;
   (iii) methylation-sensitive single nucleotide primer extension;
   (iv) methylated CpG island amplification;
   (v) the HeavyMethyl assay;
   (vi) Headloop PCR;
   (vii) the Helper-dependent chain reaction;
   (viii) pyrosequencing; or
   (ix) Melting curve analysis.

3. The method according to claim 1, wherein said neoplasm is an adenoma, an adenocarcinoma, or a colorectal neoplasm.

4. A method for detecting the onset, or predisposition to the onset, of a large intestine neoplasm in a human subject, said method comprising:
   assessing the methylation level of CpG dinucleotides in SEQ ID NO: 3 and/or the complement thereof in a free circulating plasma DNA sample from said subject;
   wherein said assessing comprises obtaining DNA from the sample, bisulfate conversion of the obtained DNA, and amplification of converted SEQ ID NO: 3 and/or the complement thereof with primers SEQ ID NO: 13 and 14;
   comparing the assessed methylation level to a methylation level of CpG dinucleotides in SEQ ID NO: 3 and/or the complement thereof in a large intestine tissue sample or free circulating plasma DNA sample from a human subject that does not have a large intestine neoplasm;
   detecting a higher level of CpG methylation in the assessed methylation level as compared to the methylation level of CpG dinucleotides in SEQ ID NO: 3 and/or the complement thereof in a large intestine tissue sample or free circulating plasma DNA from a human subject that does not have a large intestine neoplasm; and
   correlating the higher level of CpG methylation in the assessed methylation status with the onset, or predisposition to the onset, of a large intestine neoplasm in the subject.

5. The method according to claim 4, wherein assessing the methylation level of CpG dinucleotides in SEQ ID NO: 3 and/or the complement thereof comprises:
   (i) methylation-specific PCR;
   (ii) the MethyLight assay;
   (iii) methylation-sensitive single nucleotide primer extension;
   (iv) methylated CpG island amplification;
   (v) the HeavyMethyl assay;
   (vi) Headloop PCR;
   (vii) the Helper-dependent chain reaction;
   (viii) pyrosequencing; or
   (ix) Melting curve analysis.

6. The method according to claim 4, wherein said neoplasm is an adenoma, an adenocarcinoma, or a colorectal neoplasm.

7. A method for detecting the onset, or predisposition to the onset, of a large intestine neoplasm in a human subject, said method comprising:
   assessing the methylation level of CpG dinucleotides in SEQ ID NO: 4 and/or the complement thereof in a free circulating plasma DNA sample from said subject;
   wherein said assessing comprises obtaining DNA from the sample, bisulfite conversion of the obtained DNA, and amplification of converted SEQ ID NO: 4 and/or the complement thereof with primers SEQ ID NO: 13 and 15;
   comparing the assessed methylation level to a methylation level of CpG dinucleotides in SEQ ID NO: 4 and/or the complement thereof in a large intestine tissue sample or free circulating plasma DNA sample from a human subject that does not have a large intestine neoplasm;
   detecting a higher level of CpG methylation in the assessed methylation level as compared to the methylation level of CpG dinucleotides in SEQ ID NO: 4 and/or the complement thereof in a large intestine tissue sample or free circulating plasma DNA from a human subject that does not have a large intestine neoplasm; and
   correlating the higher level of CpG methylation in the assessed methylation status with the onset, or predisposition to the onset, of a large intestine neoplasm in the subject.

8. The method according to claim 7, wherein assessing the methylation level of CpG dinucleotides in SEQ ID NO: 4 and/or the complement thereof comprises:
   (i) methylation-specific PCR;
   (ii) the MethyLight assay;
   (iii) methylation-sensitive single nucleotide primer extension;
   (iv) methylated CpG island amplification;
   (v) the HeavyMethyl assay;
   (vi) Headloop PCR;
   (vii) the Helper-dependent chain reaction;
   (viii) pyrosequencing; or
   (ix) Melting curve analysis.

9. The method according to claim 7, wherein said neoplasm is an adenoma, an adenocarcinoma, or a colorectal neoplasm.

* * * * *

UNITED STATES PATENT AND TRADEMARK OFFICE
CERTIFICATE OF CORRECTION

PATENT NO. : 10,526,642 B2
APPLICATION NO. : 14/240734
DATED : January 7, 2020
INVENTOR(S) : Peter Laurence Molloy et al.

It is certified that error appears in the above-identified patent and that said Letters Patent is hereby corrected as shown below:

On the Title Page

In Column 2, item (56), Other Publications, Line 16, delete "orinted" and insert -- oriented --.

On page 2, in Column 1, item (56), Other Publications, Line 19, delete "Biocehm.," and insert -- Biochem., --.

In the Specification

In Column 1, Line 44, delete "nucleic-acid" and insert -- nucleic acid --.

In Column 3, Line 5, delete "is" and insert -- it --.

In Column 5, Line 57, delete "eg." and insert -- e.g. --.

In Column 6, Line 49, delete "intestine, or" and insert -- intestine or --.

In Column 8, Line 6, delete "location-numbering" and insert -- location numbering --.

In Column 8, Line 56, delete "acinii" and insert -- acini --.

In Column 10, Line 22 approx., delete "e" and insert -- c --.

In Column 10, Line 22 approx., delete "e" and insert -- c --.

In Column 10, Line 22 approx., delete "e" and insert -- c --.

In Column 11, Line 8, delete "neoplasias," and insert -- neoplasia, --.

In Column 12, Line 26, delete "methylstransferase" and insert -- methyltransferase --.

Signed and Sealed this
Second Day of June, 2020

Andrei Iancu
*Director of the United States Patent and Trademark Office*

CERTIFICATE OF CORRECTION (continued)
U.S. Pat. No. 10,526,642 B2

In Column 12, Line 43, delete "value."" and insert -- value". --.

In Column 13, Line 52, delete "ID-NOs:" and insert -- ID NOs: --.

In Column 14, Line 36, delete "eg." and insert -- e.g. --.

In Column 16, Line 2, delete "neoplasias." and insert -- neoplasia. --.

In Column 19, Line 23, delete "Taqman" and insert -- TaqMan --.

In Column 22, Line 1, delete "lightcycler" and insert -- LightCycler --.

In Column 22, Line 22, delete "RNaseH" and insert -- RNase H --.

In Column 22, Line 43, delete "$^{3}2P$)." and insert -- $^{32}P$). --.

In Column 22, Line 48, delete "electrophoresis." and insert -- electrophoresis --.

In Column 22, Line 67, delete "DNaseI" and insert -- DNase I --.

In Column 23, Line 52, delete "amplified," and insert -- amplified --.

In Column 24, Line 30, delete "for example." and insert -- for example, --.

In Column 24, Line 36, delete "(Me-SnuPE)" and insert -- (Ms-SNuPE) --.

In Column 27, Line 61, delete "invention" and insert -- invention. --.

In Column 27, Line 67, delete "MethylLight" and insert -- MethyLight --.

In Column 28, Line 16, delete "Taq DNA" and insert -- TaqDNA --.

In Column 28, Line 50, delete "particular." and insert -- particular --.

In Column 28, Line 51, delete "rhodomine" and insert -- rhodamine --.

In Column 29, Line 45, delete "1997)," and insert -- 1997, --.

In Column 36, Line 24, delete "Os" and insert -- as --.

In Column 36, Line 58, delete "neoplasias" and insert -- neoplasia --.

In Column 42, Line 34-35, delete "SybrGreen)," and insert -- SYBR Green), --.

In Column 42, Line 36, delete "(1" and insert -- 1 --.

CERTIFICATE OF CORRECTION (continued)
U.S. Pat. No. 10,526,642 B2

In Column 43, Line 45, delete "ie" and insert -- i.e. --.

In Column 43, Line 46, delete "hg19" and insert -- Hg19 --.

In Column 43, Line 65, delete "MgCl2" and insert -- $MgCl_2$ --.

In Column 43, Line 66, delete "uM" and insert -- μM --.

In Column 44, Line 37, delete "Ix Platinum" and insert -- 1x Platinum --.

In Column 45, Line 34 approx., delete "L" and insert -- μL --.

In Column 47, Line 7, delete "(Nucl." and insert -- Nucl. --.

In Column 47, Line 28, delete "(In:" and insert -- In: --.

In the Claims

In Column 59, Line 9, Claim 1, delete "bisulfate" and insert -- bisulfite --.

In Column 59, Line 52, Claim 4, delete "bisulfate" and insert -- bisulfite --.